US008839672B2

(12) United States Patent
Emelianov et al.

(10) Patent No.: US 8,839,672 B2
(45) Date of Patent: Sep. 23, 2014

(54) COMBINED ULTRASOUND AND PHOTOACOUSTIC IMAGING OF METAL OBJECTS

(75) Inventors: Stanislav Emelianov, Austin, TX (US); Jimmy Su, Austin, TX (US); Bo Wang, Austin, TX (US); Andrei Karpiouk, Austin, TX (US); Yun-Sheng Chen, Austin, TX (US); Wolfgang Frey, Austin, TX (US); Richard Bouchard, Austin, TX (US); Kimberly Homan, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/277,074

(22) Filed: Oct. 19, 2011

(65) Prior Publication Data
US 2012/0253180 A1 Oct. 4, 2012

Related U.S. Application Data

(63) Continuation-in-part of application No. 13/190,344, filed on Jul. 25, 2011.

(60) Provisional application No. 61/394,642, filed on Oct. 19, 2010, provisional application No. 61/435,474, filed on Jan. 24, 2011.

(51) Int. Cl.
*G01N 29/00* (2006.01)
*A61B 8/00* (2006.01)

(52) U.S. Cl.
USPC .............................. 73/606; 73/620; 600/447

(58) Field of Classification Search
USPC ........... 73/606, 633, 649, 596; 600/407, 431, 600/437, 443, 447
See application file for complete search history.

(56) References Cited

U.S. PATENT DOCUMENTS

| 6,167,297 A * | 12/2000 | Benaron ...................... 600/431 |
| 6,216,540 B1 * | 4/2001 | Nelson et al. .................. 73/633 |
| 6,246,901 B1 * | 6/2001 | Benaron ...................... 600/431 |
| 6,638,224 B2 * | 10/2003 | Ohtsuki et al. ................ 600/443 |
| 7,668,587 B2 * | 2/2010 | Benaron et al. ............... 600/476 |
| 8,364,414 B2 * | 1/2013 | Masumura ...................... 702/19 |
| 2005/0187471 A1 * | 8/2005 | Kanayama et al. ........... 600/437 |
| 2006/0184042 A1 * | 8/2006 | Wang et al. ................... 600/476 |
| 2008/0154130 A1 * | 6/2008 | Weiss et al. ................... 600/437 |
| 2009/0054763 A1 * | 2/2009 | Wang et al. ................... 600/425 |
| 2010/0049044 A1 * | 2/2010 | Burcher ........................ 600/437 |
| 2010/0074845 A1 * | 3/2010 | Gambhir et al. .............. 424/9.1 |

OTHER PUBLICATIONS

D. Maintz, R. M. Botnar, R. Fischbach, W. Heindel, W. J. Manning, and M. Stuber, "Coronary magnetic resonance angiography for assessment of the stent lumen: a phantom study," J. Cardiovasc. Magn. Reson. 4(3), 359-367 (2002).

(Continued)

*Primary Examiner* — J M Saint Surin
(74) *Attorney, Agent, or Firm* — Baker Botts L.L.P.

(57) ABSTRACT

Methods of combined ultrasound and photoacoustic imaging are provided. In some embodiments, the methods may be used to determine the location or positioning of a metal object in a sample. In other embodiments, the methods may be used to determine the composition of a sample surrounding a metal object. Other methods are also provided.

19 Claims, 19 Drawing Sheets

(56) References Cited

OTHER PUBLICATIONS

D. R. Elgort, C. M. Hillenbrand, S. Zhang, E. Y. Wong, S. Rafie, J. S. Lewin, and J. L. Duerk, "Image-guided and -monitored renal artery stenting using only MRI," J. Magn. Reson. Imaging 23(5), 619-627 (2006).

J. Hug, E. Nagel, A. Bornstedt, B. Schnackenburg, H. Oswald, and E. Fleck, "Coronary arterial stents: safety and artifacts during MR imaging," Radiology 216(3), 781-787 (2000).

D. Maintz, K. U. Juergens, T. Wichter, M. Grude, W. Heindel, and R. Fischbach, "Imaging of coronary artery stents using multislice computed tomography: in vitro evaluation," Eur. Radiol. 13(4), 830-835 (2003).

Y. Kawase, K. Hoshino, R. Yoneyama, J. McGregor, R. J. Hajjar, I. K. Jang, and M. Hayase, "In vivo volumetric analysis of coronary stent using optical coherence tomography with a novel balloon occlusionflushing catheter: a comparison with intravascular ultrasound," Ultrasound Med. Biol. 31(10), 1343-1349 (2005).

G. S. Mintz, S. E. Nissen, W. D. Anderson, S. R. Bailey, R. Erbel, P. J. Fitzgerald, F. J. Pinto, K. Rosenfield, R. J. Siegel, E. M. Tuzcu, and P. G. Yock, "American College of Cardiology Clinical Expert Consensus Document on Standards for Acquisition, Measurement and Reporting of Intravascular Ultrasound Studies (IVUS). A report of the American College of Cardiology Task Force on Clinical Expert Consensus Documents," J. Am. Coll. Cardiol. 37(5), 1478-1492 (2001).

P. Barlis, K. Dimopoulos, J. Tanigawa, E. Dzielicka, G. Ferrante, F. Del Furia, and C. Di Mario, "Quantitative analysis of intracoronary optical coherence tomography measurements of stent strut apposition and tissue coverage," Int. J. Cardiol (2009).

T. L. Slottow, R. Pakala, T. Okabe, D. Hellinga, R. J. Lovec, F. O. Tio, A. B. Bui, and R. Waksman, "Optical coherence tomography and intravascular ultrasound imaging of bioabsorbable magnesium stent degradation in porcine coronary arteries," Cardiovasc. Revasc. Med. 9(4), 248-254 (2008).

I. K. Jang, B. E. Bouma, D. H. Kang, S. J. Park, S. W. Park, K. B. Seung, K. B. Choi, M. Shishkov, K. Schlendorf, E Pomerantsev, S. L. Houser, H. T. Aretz, and G. J. Tearney, "Visualization of coronary atherosclerotic plaques in patients using optical coherence tomography: comparison with intravascular ultrasound," J. Am. Coll. Cardiol. 39(4), 604-609 (2002).

S. Sethuraman, S. R. Aglyamov, J. H. Amirian, R. W. Smalling, and S. Y. Emelianov, "Intravascular photoacoustic imaging using an IVUS imaging catheter," IEEE Trans. Ultrason. Ferroelectr. Freq. Control 54(5), 978-986 (2007).

S. Sethuraman, J. H. Amirian, S. H. Litovsky, R. W. Smalling, and S. Y. Emelianov, "Ex vivo Characterization of Atherosclerosis using Intravascular Photoacoustic Imaging," Opt. Express 15(25), 16657-16666 (2007).

S. Sethuraman, J. H. Amirian, S. H. Litovsky, R. W. Smalling, and S. Y. Emelianov, "Spectroscopic intravascular photoacoustic imaging to differentiate atherosclerotic plaques," Opt. Express 16(5), 3362-3367 (2008).

J. Butany, K. Carmichael, S. W. Leong, and M. J. Collins, "Coronary artery stents: identification and evaluation," J. Clin. Pathol. 58(8), 795-804 (2005).

B. Wang, A. B. Karpiouk, and S. Y. Emelianov, "Design of catheter for combined intravascular photoacoustic and ultrasound imaging". Proceedings of the 2008 IEEE Ultrasonics Symposium 1150-1153 (2008).

D. J. Faber, M. C. Aalders, E. G. Mik, B. A. Hooper, M. J. van Gemert, and T. G. van Leeuwen, "Oxygen saturation-dependent absorption and scattering of blood," Phys. Rev. Lett. 93(2), 028102 (2004).

J. W. Charboneau, C. C. Reading, and T. J. Welch, "CT and sonographically guided needle biopsy: current techniques and new innovations," Am. J. Roentgenol. 154, 1-10 (1990).

G. A. Chapman, D. Johnson, and A. R. Bodenham, "Visualisation of needle position using ultrasonography," Anaesthesia 61, 148-158 (2006).

K. J. Chin, A. Perlas, V. W. Chan, and R. Brull, "Needle visualization in ultrasound-guided regional anesthesia: challenges and solutions," Reg. Anesth. Pain Med. 33, 532-544 (2008).

N. Abolhassani, R. V. Patel, and F. Ayazi, "Minimization of needle deflection in robot-assisted percutaneous therapy," Int J. Med. Robot 3, 140-148 (2007).

S. Nath, Z. Chen, N. Yue, S. Trumpore, and R. Peschel, "Dosimetric effects of needle divergence in prostate seed implant using 125I and 103Pd radioactive seeds," Med. Phys. 27, 1058-1066 (2000).

I. Schafhalter-Zoppoth, C. E. McCulloch, and A. T. Gray, "Ultrasound visibility of needles used for regional nerve block: an in vitro study," Reg. Anesth. Pain Med. 29, 480-488 (2004).

T. Hatada, H. Ishii, S. Ichii, K. Okada, and T. Yamamura, "Ultrasound-guided fine-needle aspiration biopsy for breast tumors: needle guide versus freehand technique," Tumori 85, 12-14 (1999).

P. M. Phal, D. M. Brooks, and R. Wolfe, "Sonographically guided biopsy of focal lesions: a comparison of freehand and probe-guided techniques using a phantom," Am. J. Roentgenol. 184, 1652-1656 (2005).

M. C. Ziskin, D. I. Thickman, N. J. Goldenberg, M. S. Lapayowker, and J. M. Becker, "The comet tail artifact," J. Ultrasound Med. 1, 1-7 (1982).

A. Gronningsaeter, T. Lie, K. Bolz, and A. Heimdal, "Ultrasonographic stent-imaging artifacts," J. Vasc. Invest. 1, 140-149 (1995).

G. Finet, C. Cachard, P. Delachartre, E. Maurincomme, and J. Beaune, "Artifacts in intravascular ultrasound imaging during coronary artery stent implantation," Ultrasound Med. Biol. 24, 793-802 (1998).

K. Homan, J. Shah, S. Gomez, H. Gensler, A. B. Karpiouk, L. Brannon-Peppas, and S. Y. Emelianov, "Combined ultrasound and photoacoustic imaging of pancreatic cancer using nanocage contrast agents," in Proc. 2009 SPIE Photonics West Symposium: Photons Plus Ultrasound: Imaging and Sensing, Proc. SPIE 71771M, (2009).

S. Mallidi, T. Larson, J. Tam, P. P. Joshi, A. Karpiouk, K. Sokolov, and S. Emelianov, "Multiwavelength photoacoustic imaging and plasmon resonance coupling of gold nanoparticles for selective detection of cancer," Nano Lett. 9, 2825-2831 (2009).

S. Park, S. R. Aglyamov, W. G. Scott, and S. Y. Emelianov, "Strain imaging using conventional and ultrafast ultrasound imaging: numerical analysis," IEEE Trans. Ultrason. Ferroelectr. Freq. Control 54, 987-995 (2007).

T. Varghese and J. Ophir, "An analysis of elastographic contrast-to-noise ratio," Ultrasound Med. Biol. 24, 915-924 (1998).

S. Sethuraman, J. H. Amirian, S. H. Litovsky, R. W. Smalling, and S. Y. Emelianov, "Spectroscopic intravascular photoacoustic imaging to differentiate atherosclerotic plaques," Opt. Express 16, 3362-3367 (2008).

J. Butany, K. Carmichael, S. W. Leong, and M. J. Collins, "Coronary artery stents: identification and evaluation," J. Clin. Pathol. 58, 795-804 (2005).

Z. Wei, M. Ding, D. Downey, and A. Fenster, "3D TRUS guided robot assisted prostate brachytherapy," Med. Image Comput. Comput. Assist. Interv. 8, 17-24 (2005).

J. L. Su, B. Wang, and S. Y. Emelianov, "Photoacoustic imaging of coronary artery stents," Opt. Express 17, 19894-19901 (2009).

M. Morooka, K. Kubota, Y. Kono, K. Ito, K. Kurihara, T. Mitsumoto, T. Sato, Y. Oshiro, T. Aruga, K. Hasuo, M. Kanemura, and S. Minowada, "Scintigraphic detection of I-125 seeds migration after permanent brachytherapy for prostate cancer: how far do seeds travel?," Clin. Nucl. Med. 34, 466-469 (2009).

M. Tavakoli, E. J. Kellar, D. Nassiri, and A. E. Joseph, "A novel polymeric coating for enhanced ultrasound visibility of medical devices," Med Device Technol 17, 8-10, 12, (2006).

\* cited by examiner

FIGURE 1A	FIGURE 1B
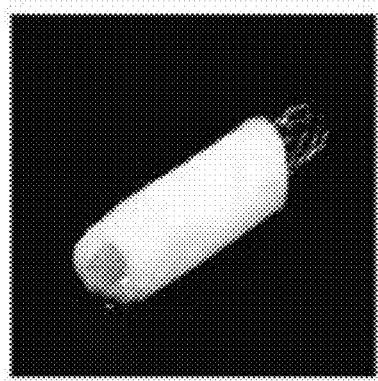 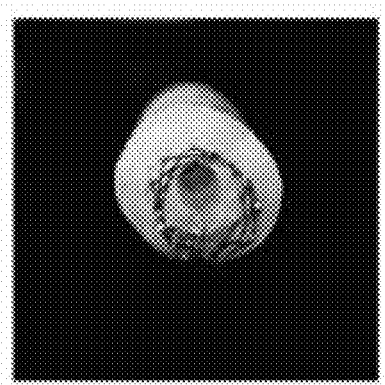
FIGURE 2
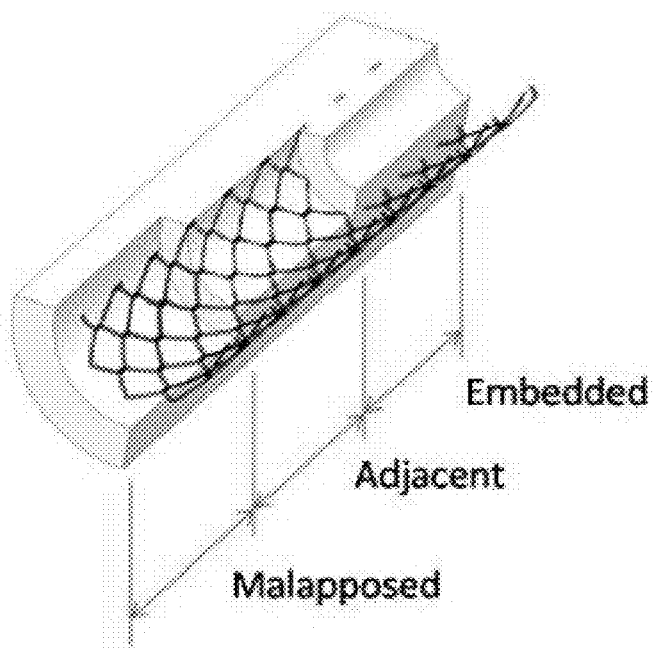

COMBINED ULTRASOUND AND PHOTOACOUSTIC IMAGING OF METAL OBJECTS

CROSS-REFERENCE TO RELATED APPLICATIONS

This application claims the benefit of U.S. Provisional Patent Application Ser. Nos. 61/394,642 filed Oct. 19, 2010 and 61/435,474, filed Jan. 24, 2011, and is a continuation-in-part of U.S. patent application Ser. No. 13/190,334, filed Jul. 25, 2011, the entire disclosures of which are incorporated by reference.

STATEMENT OF GOVERNMENT INTEREST

This invention was made with government support under Grant Number HL096981 awarded by the National Institutes of Health. The government has certain rights in the invention.

BACKGROUND

A wide variety of metal implants are used clinically within the human body. These range from permanently implanted metals such as orthopedic replacements, coronary arterial stents, or brachytherapy seeds, and include temporarily implanted metals such as surgical staples.

Hypodermic needles are one such temporary metal implant used for a wide variety of clinical applications. Metal needles are commonly used for localized drug delivery, such as in cancer therapy, or for tissue collection in biopsy. In either case, the ability to visualize both the anatomical surrounding structures and the advancing needle tip is required. Several procedures, such as drug delivery, tissue biopsy collection, or brachytherapy seed placement, all require accurate injection of a metal needle. Needle tracking also requires the visualization of the tissue background so that specific tissue landmarks such as tumors or lesions may be targeted or avoided when guiding the needle into position. Needle deflection and deformation can occur when inserting needles into soft, non-homogeneous tissues, which can affect the localized accuracy of insertion.

Currently, the most commonly used clinical strategy to visualize the direction of the needle shaft in real time is ultrasound guidance. However, the needle tip can often be visualized better than the needle shaft because of the irregular surface of the machine-cut bevel, which scatters the ultrasound (US) beam in all directions, reflecting the beam, in part, back to the transducer. However, visibility of the tip alone is not sufficient for the clinician to gauge the insertion angle of the needle. Visibility of the needle shaft is dependent on the angle of the needle relative to the transducer and is best visualized only when perpendicular and in the plane of the US transducer. Needle deflections away from the transducer of only a few degrees are usually enough to conceal the US signal from the needle. To overcome these issues, mechanical or optical needle guides are often used to keep the needle in the transducer plane. However, these guides restrict needle movement when fine adjustments are needed by medical operators; therefore, many clinicians prefer using a freehand technique during needle insertion and injection.

US imaging of metal needles also produces an unexpected echographic pattern resembling the shape of a comet tail. The pattern is due to reverberations within the needle and is dependent on the acoustic impedance mismatch between the needle and its surroundings. In fact, these artifacts are present in US imaging of any metallic object. While these artifacts can be helpful in determining the presence of foreign metal in vivo, the existence of the comet tail pattern prevents visibility of objects directly distal and adjacent to the needle (relative to the position of the transducer). This effect can detrimentally affect the ability to determine needle position relative to the background tissue.

Likewise, when using current ultrasound technology to track needle insertions/interventions, tissue background has been determined through the ultrasound speckle shown on the imaging screen. However, the acoustic speckle between different tissue compositions does not always offer enough contrast in order to determine what tissue landmarks the needle tip has penetrated to. Though photoacoustic imaging can utilize optical absorption to differentiate tissue types, some tissues have very low absorption and therefore may have very low signals when imaged under photoacoustic imaging. The difference in acoustic scattering between healthy and diseased tissue is not usually very high. Therefore, needle trajectories can oftentimes miss the region of interest that the operator is interested in when basing decisions on ultrasound alone. Furthermore, when targeting needle interventions into soft tissue, the real-time imaging modality should confirm the arrival of the needle into the region of interest. Without confirmation of needle arrival, false negatives can occur when conducting biopsies.

Current technologies only allow for needle tracking with limited to no tissue characterization. In ultrasound, only landmarks that contain strong differences in acoustic scattering can be differentiated. Similarly, in photoacoustic imaging alone, only tissue with strong optical absorption can be visualized. For example, fat is not easily differentiated from muscle in ultrasound, nor does it have a high absorption for visualization in photoacoustics.

In addition to temporary metal implants, permanent metal implants, such as coronary arterial stents, are also used clinically within the human body. Coronary stents are currently the most widely used coronary intervention in the United States. While the procedure is more than 95% successful, stents have brought along several unique issues including restenosis, hyperplasia and stent drift. The ability to visualize stents both during the stenting procedure and during post-surgery follow-up is important in order to correctly assess the stent with respect to the plaques and vessel, and also identify its apposition within the vessel wall.

Immediately following a stenting procedure, it is important to determine the relation of the stent struts to the vessel wall. Ideally, the stent is deployed in contact with the lumen wall; however, malapposition can occur resulting in the stent detaching itself from the wall. This detachment can cause turbulent eddies to form in the vessel which can lead to thrombosis in the area of the stent. It is important when monitoring the stent to determine how much restenosis has formed around the stent struts. The distance that the stent struts are embedded into the vessel wall must be determined to assess stent viability.

Currently, the most common method for assessing stent position is x-ray coronary angiography/fluoroscopy. However, this procedure is problematic due to its use of ionizing radiation and possible complications in using iodinated contrast agents. Furthermore, x-ray fluoroscopy can only depict a two-dimensional projection which can lead to an underestimation of lumen diameter and the stent apposition within the lumen.

Magnetic resonance imaging has been used to image stents due to its avoidance of radiation exposure and iodine contrast agents; however, the metallic composition of stents can cause susceptibility artifacts which can obscure the stent lumen and make it very difficult to visualize the relation between the stent and the vessel wall. Long scan times and low resolution also remain a major limitation. Multi-slice computed tomographic angiography (MSCTA) has been shown to image much faster than MRI; however, its low resolution and artifacts in metallic stents make assessing the surrounding vessel difficult.

Both intravascular ultrasound (IVUS) and optical coherence tomography (OCT) have reached widespread usage in catheterization labs. IVUS can detect signal reflections from the stent struts, but has insufficient contrast to determine the struts' position against the vessel wall. Ultrasound contrast of stents is affected by the background tissue environment, which is also acoustically scattering. In addition, extraneous beams of ultrasound generated by the ultrasound transmit pulse and then scattered by the metallic stents will obscure the edges of the stent borders. These blurred edges are image artifacts that can reduce the spatial registration of the imaged stent. OCT directly competes with these disadvantages with a resolution of 10-20 µm but has severe depth limitations, allowing only a penetration depth of about 2 mm. The presence of blood flowing through the vessel limits this depth even further, requiring clinicians to flush the vessel during the imaging procedure. Furthermore, the tissue behind the stent strut becomes hidden due to scattering shadows in OCT, which prevents complete diagnosis of the stent's relation to the vessel lumen.

SUMMARY

The present disclosure generally relates to ultrasound and photoacoustic imaging. More particularly, the present disclosure relates to combined ultrasound and photoacoustic imaging of objects comprising metal.

In one embodiment, the present disclosure provides a method comprising generating a photoacoustic image of at least a portion of a sample comprising a metal object; generating an ultrasound image of at least the portion of the sample comprising the metal object; and determining the location or positioning of the metal object within the sample by using an overlay of the photoacoustic image and the ultrasound image.

In another embodiment, the present disclosure provides a method comprising exposing at least a portion of a sample comprising a metal object to electromagnetic radiation so as to generate an acoustic response; detecting the acoustic response with an acoustic sensor; generating a photoacoustic image of at least the portion of the sample comprising the metal object based on the acoustic response detected by the acoustic sensor; exposing at least a portion of the sample comprising the metal object to an acoustic sound wave so as to generate an echo; detecting the echo with the acoustic sensor; and generating an ultrasound image of at least the portion of the sample comprising the metal object based on the echo detected by the acoustic sensor.

In yet another embodiment, the present disclosure provides a method comprising generating a photoacoustic image of at least a portion of a sample comprising a metal object; generating an ultrasound image of at least the portion of the sample comprising the metal object; and employing a filtering technique so as to at least partially remove or reduce an echographic pattern due to acoustic reverberation from the photoacoustic or ultrasound image.

The features and advantages of the present invention will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

FIGS. 1A and 1B are photographs of the first vessel mimicking phantom with a stent embedded in the lumen wall. A 5.0 mm inner diameter stainless steel stent was molded 1 mm deep within the vessel wall from the lumen. An 8 mm long region of the stent was left bare outside of the phantom vessel, which was constructed from 8% cross-linked polyvinyl alcohol (PVA).

FIG. 2 is a cut-away diagram of the second vessel phantom consisting of three regions of varying distances between the stent and the vessel wall to model embedded (within the vessel wall), deployed (adjacent to the vessel wall), and malapposed (separate from the vessel wall) stents.

Figures 3A, 3B, 3C:
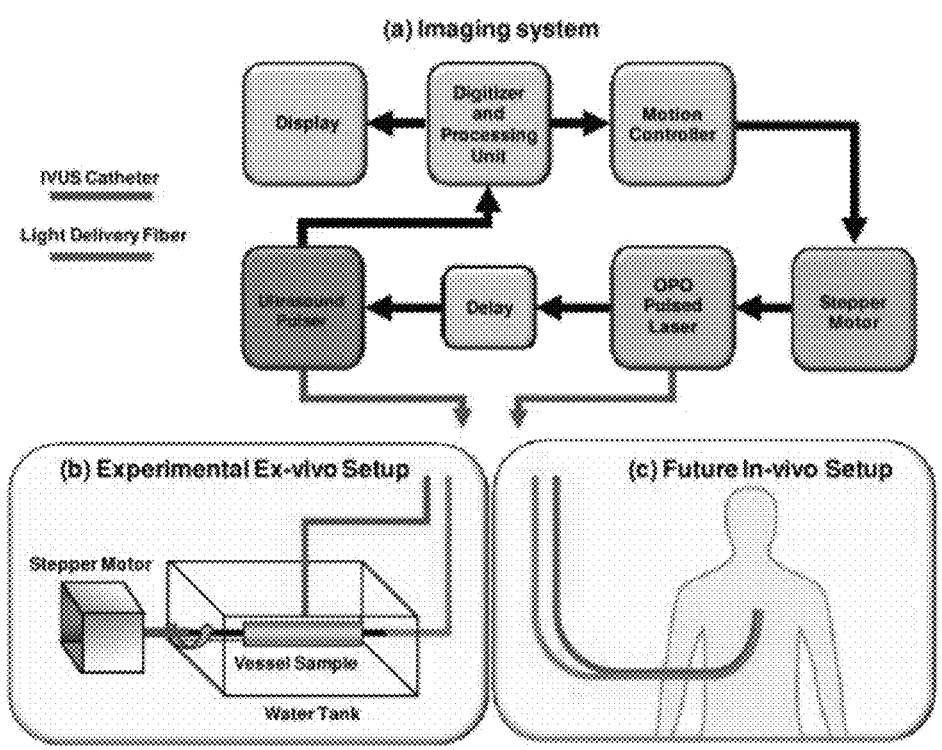
FIG. 3A is an image depicting an overall IVUS/IVPA imaging system, according to one embodiment.

FIG. 3B is an ex-vivo prototype photoacoustic imaging setup, according to one embodiment. The vessel was placed in a water tank and externally illuminated using an optical fiber. The ultrasound imaging catheter was placed inside the lumen and the vessel was rotated incrementally as IVUS/IVPA A-lines were collected.

FIG. 3C is a diagram of an integrated IVUS/IVPA imaging catheter where the IVUS probe and fiber-optical light delivery system are combined for in-vivo intravascular imaging.

Figures 4A, 4B, 4C:
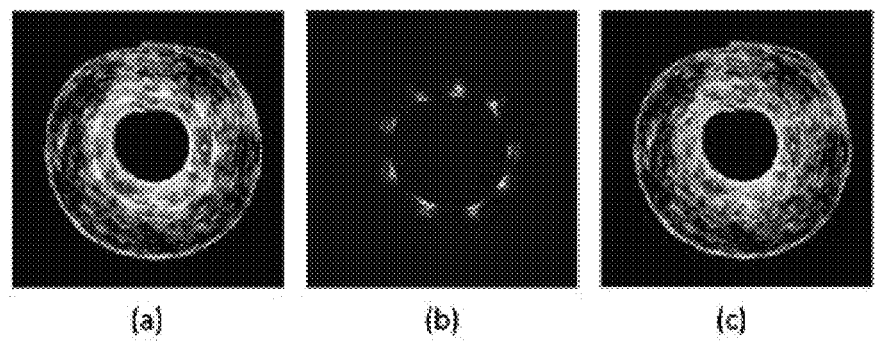

FIG. 4A is an ultrasound (IVUS) cross-sectional image of the stent deployed within the vessel phantom.

FIG. 4B is a photoacoustic (IVPA) cross-sectional image of the stent deployed within the vessel phantom.

FIG. 4C is an overlay of the two images shown in FIGS. 4A and 4B, which together show the position of the stent struts with respect to the thickness of the vessel wall.

Figures 5A, 5B, 5C:
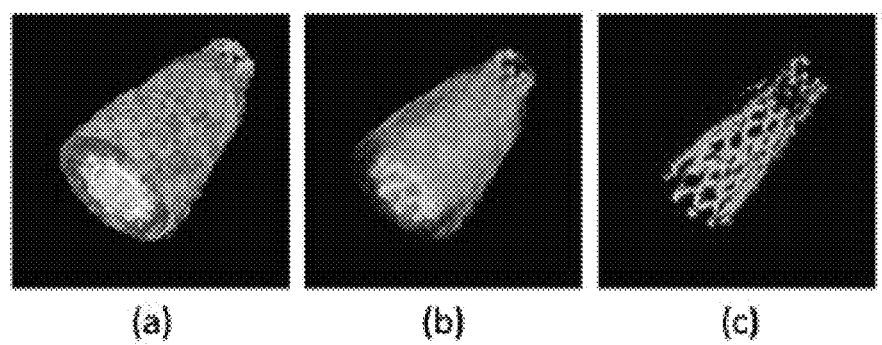

FIGS. 5A-5C are three-dimensional (3D) reconstructions of the vessel and stent. The 3D images were created by acquiring a stack of cross-sectional images and combining them together. The ultrasound and photoacoustic signals can be displayed with different transparency in the reconstructed image to show the position and shape of the stent within the vessel.

Figures 6A, 6B, 6C:
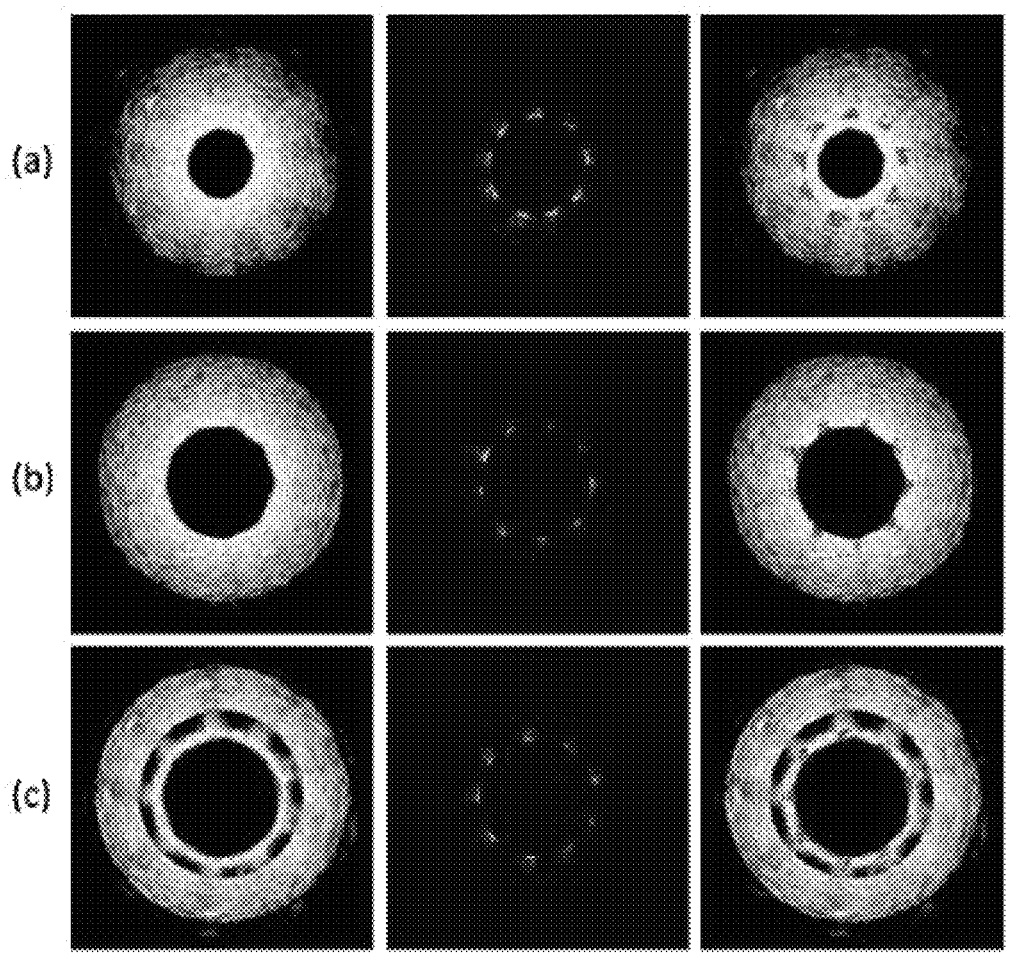

FIGS. 6A-6C are intravascular ultrasound and photoacoustic and combined IVUS/IVPA images from the three different regions in the stented vessel. (A) Stent embedded within the vessel. (B) Stent adjacent to lumen wall. (C) Stent detached from lumen wall.

FIGS. 7A-7D are 3D-reconstructions of the tri-sectional phantom. Individual cross sections can show the position of the stent within the vessel. (A) Ultrasound 3D reconstruction of the phantom showing the structure of the vessel. (B) Photoacoustic reconstruction of the stent structure which can be used to assess the condition of the stent. (C) Photoacoustic image of the stent overlaid with the ultrasound image of the vessel can show the position of both. (D) Cut-away image of the reconstruction, allowing for accurate assessment of the stent within the vessel.

Figure 8:
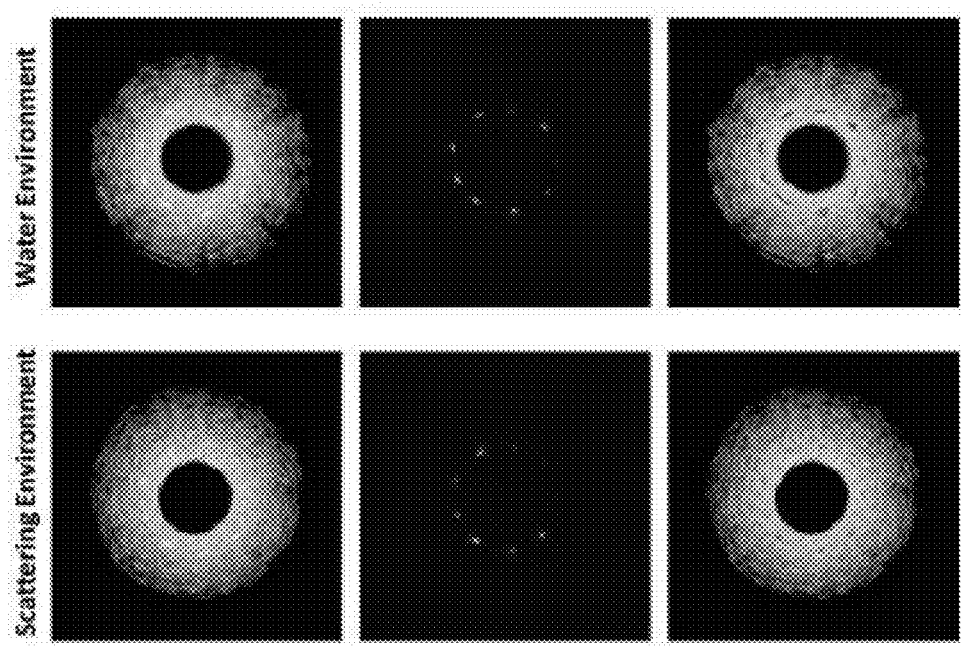

FIG. 8 is IVUS/IVPA imaging of vessel-mimicking phantom in transparent (i.e. non-scattering) and scattering medium. Ultrasound images displayed at 55 dB. Photoacoustic images in water and scattering medium displayed at 15 dB and 10 dB, respectively.

Figure 9:
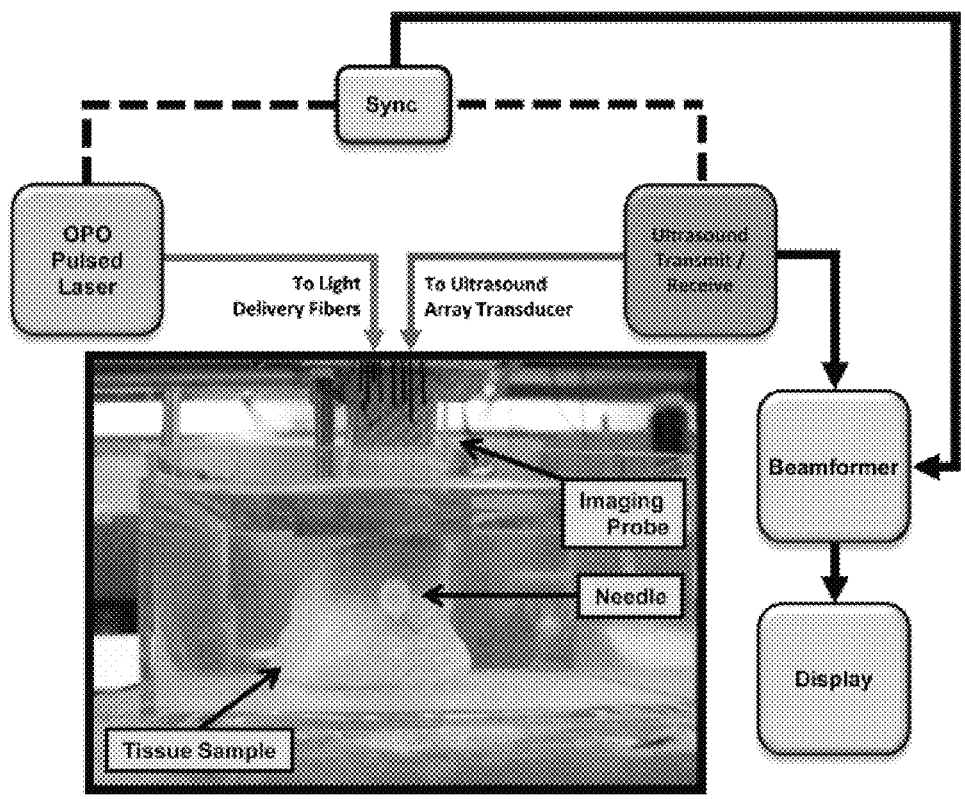

FIG. 9 is an image depicting an experimental setup for imaging metal needles in a porcine tissue sample. An imaging probe comprising a 7-MHz linear array transducer and an 18-fiber bundle was positioned on the top of the sample. The pork sample was placed in a water tank for the purposes of acoustic coupling. The sample was irradiated at a 1064-nm wavelength. Laser fluence was approximately 10 mJ/cm$^2$.

Figure 10:

FIG. 10 is a schematic view of the 30-gauge (30 G) and 21-gauge (21 G) needles. The 30 G needle was inserted into pork loin tissue perpendicular, and later reinserted at an angle of approximately 15 deg to the surface of the US transducer. The 21 G needles were inserted at various angles relative to the US transducer.

Figure 11:
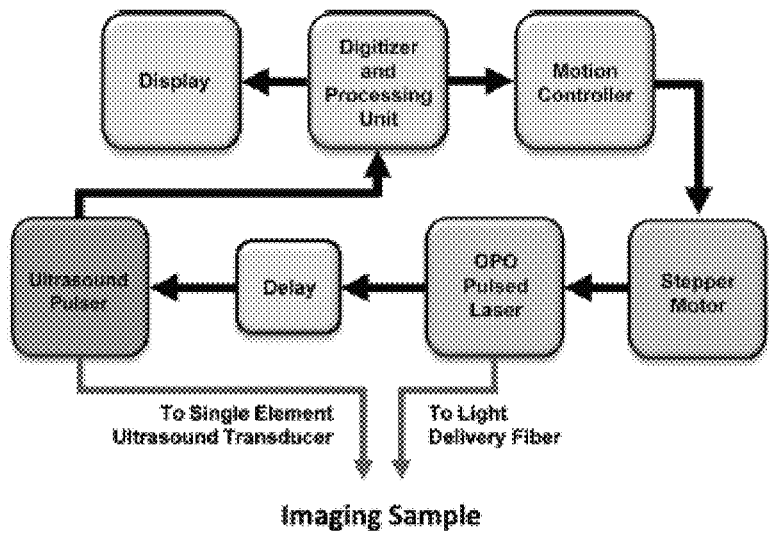

FIG. 11 is an image depicting an experimental setup for imaging of metal needles positioned at different angles in water and gelatin phantom. Imaging was performed with a single element US transducer (7 MHz, f/4). The center frequency of this transducer was similar to the imaging array used in FIG. 9. The imaging sample was irradiated with 800-nm-wavelength light. Laser fluence was also approximately 10 mJ/cm$^2$.

Figures 12A, 12B, 12C, 12D:
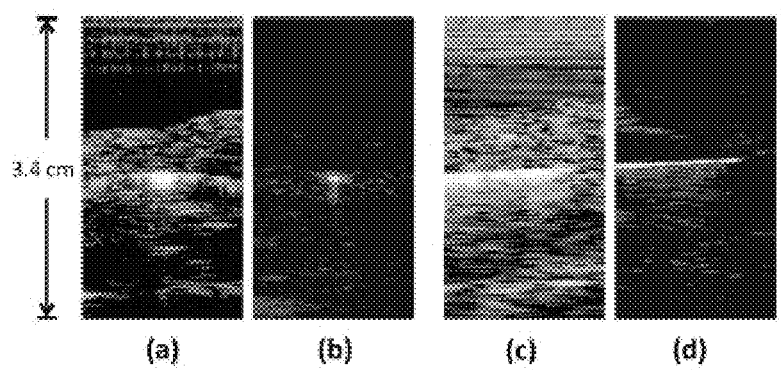

FIGS. 12A-12D are images of a hypodermic needle inserted perpendicular to the US transducer. The needle was inserted horizontally through the pork loin sample. The transducer is located toward the top of the images. FIG. 12A is an US image of the needle cross section in pork sample; FIG. 12B is a PA image of needle cross section, where the needle is easily visible; FIG. 12C is an US image of the needle and tissue in the transducer imaging plane; and FIG. 12D is a PA image of the needle in the transducer imaging plane, where the metal needle is clearly visible. The dimensions of the pork loin are approximately 30×30×30 mm$^3$. US images are displayed at 40 dB, PA images at 20 dB.

Figures 13A, 13B, 13C:
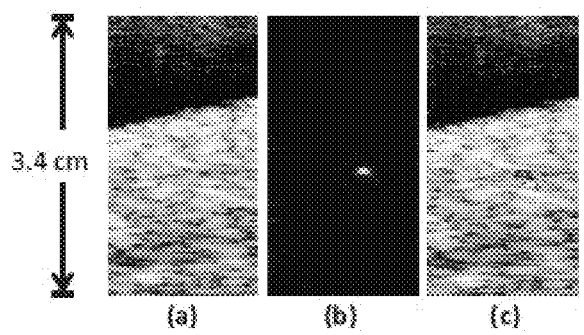

FIGS. 13A-13C are images of the hypodermic needle inserted angled approximately 15 deg with respect to horizontal. The needle is repositioned in the same tissue as in FIG. 12. The transducer is oriented at the top of the images. FIG. 13A is an US image of the tissue containing the needle cross section; the angled needle is not visible; FIG. 13B is a PA image of same cross section as FIG. 13A, the highly absorbing needle appears very clearly; FIG. 13C combined US and PA image showing the exact location of the needle within the tissue. US images are displayed at 40 dB, PA images at 20 dB. Since US and PA images are obtained at the same position, the two images are spatially coregistered.

Figures 14A, 14B:
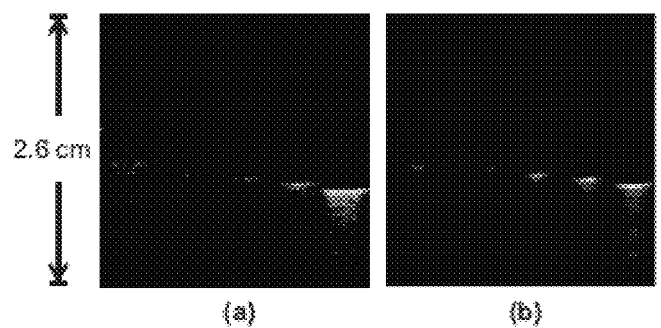

FIGS. 14A-14B are cross-sectional images of five 21 G needles in water. The needles are angled downward with respect to the horizontal plane. From left to right, needles are angled at 30, 20, 10, 5, and 0 deg, respectively.

Figures 15A, 15B:
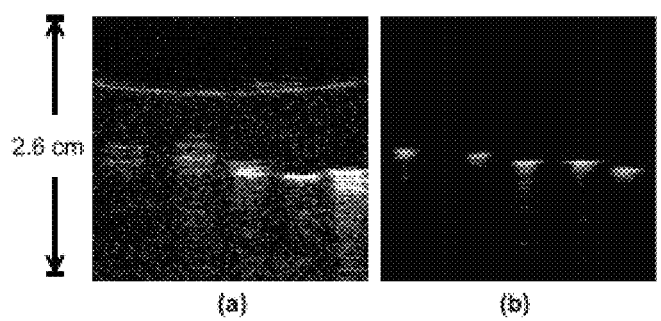

FIGS. 15A-15B are cross-sectional images of five 21 G needles inserted into a tissue-mimicking gelatin phantom containing optical scatterers. From left to right, needles are angled at 30, 20, 10, 5, and 0 deg downward with respect to the horizontal plane.

Figures 16A, 16B, 16C:
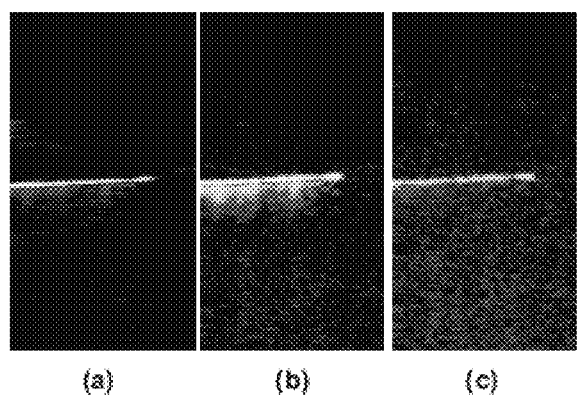

FIGS. 16A-16C are PA images from FIG. 12D showing filtering technique to remove comet-tail artifacts; FIG. 16A is an unfiltered PA image of the horizontal needle, The FFT of the signal shows one frequency peak at the center frequency of the transducer (7 MHz) and one at a lower frequency around 3 MHz, representing the signal from the comet tail; FIG. 16B is the result of bandpass filtering demonstrating incorrect choice of cut-off frequencies (3 to 10 MHz), low-frequency components are still present, blurring out the artifacts; and FIG. 16C is the correct bandpass filtering (4 to 10 MHz), which eliminated the comet-tail artifact. Contrast-to-noise ratios in FIGS. 16A, 16B and 16C were calculated to be 39.3, 38.2, and 32.5 dB, respectively.

Figures 17A, 17B:
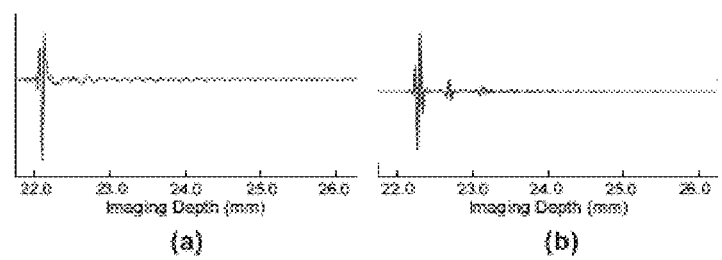

FIGS. 17A and 17B show individual A-lines of the rf signal through the needle, demonstrating the nature of the comet-tail artifact. Though the images appear similar, the underlying signals are not. FIG. 17A shows the PA A-line, the comet-tail artifact appears to be a continuous signal that diminishes over time, and FIG. 17B shows the US A-line at the same location. The comet-tail artifact in the US image appears as a discontinuous train of signal bursts that decrease in amplitude over time.

Figures 18A, 18B, 18C:
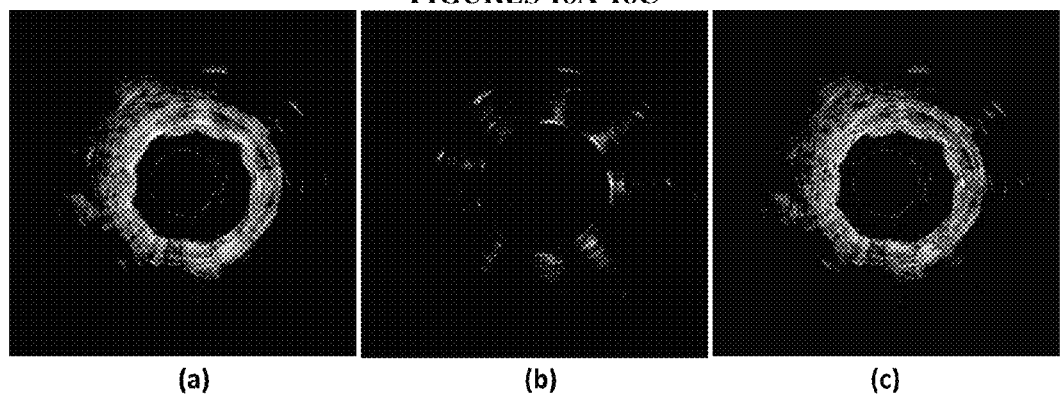

FIGS. 18A-18C show (A) ultrasound (IVUS) and (B) photoacoustic (IVPA) cross-sectional images of the stent deployed within an excised rabbit artery; (C) an overlay of the two images (A&B) together shows the position of the stent struts with respect to the thickness of the vessel wall. US and PA images are displayed at 55 dB and 25 dB, respectively.

Figures 19A, 19B:
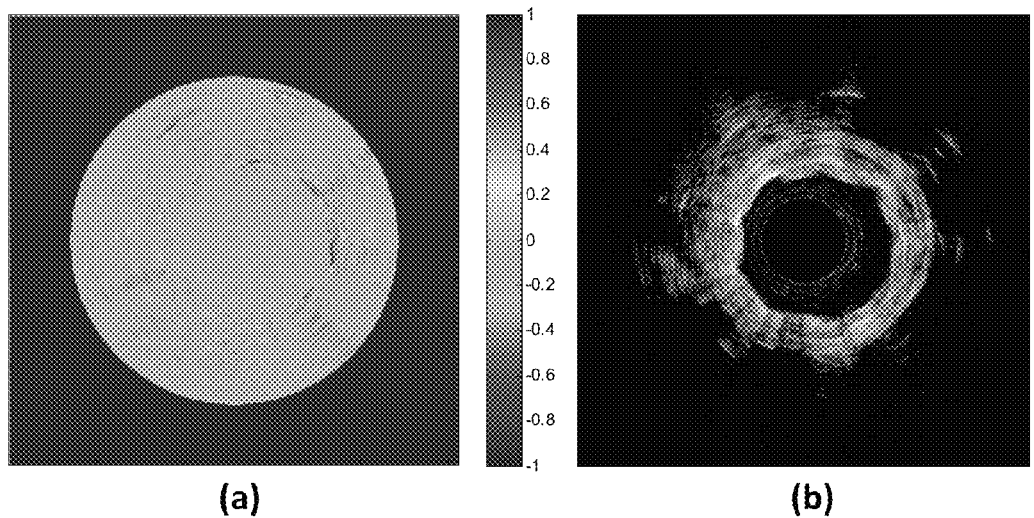

FIGS. 19A-19B show (A) a correlation colormap based on multi-wavelength PA data obtained across multiple wavelengths and (B) correlation coefficients greater than 80% are then displayed overlaid on the US cross-sectional image.

Figure 20:
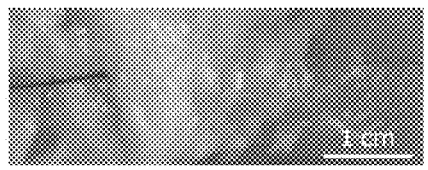

FIG. 20 is a photograph of a metal wire inserted through the fat and muscle regions of porcine tissue.

FIGS. 21A-21D show co-registered (A) ultrasound and (B) photoacoustic images of an 18-gauge needle inserted horizontally into porcine tissue; (c) ultrasound and (d) photoacoustic images of the same tissue with needle inserted at a steep angle. The needle is not visible in the ultrasound image but still visible in the photoacoustic image. Photoacoustic images are displayed at 40 dB.

Figures 22A, 22B, 22C:
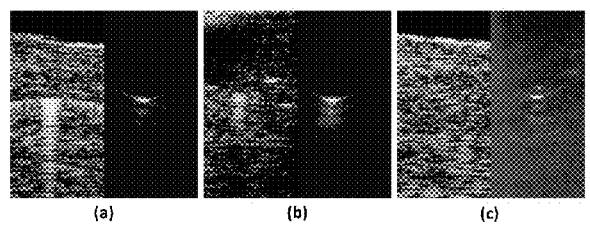

FIGS. 22A-22C show transverse images in ultrasound and photoacoustic of needle inserted into tissue; (A) Needle inserted horizontally 0°, (B) Needle at 5°, and (C) needle at 10°. At 10°, the needle is invisible in the ultrasound image.

Figure 23:
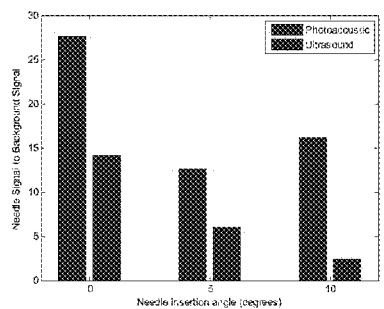

FIG. 23 is a chart depicting the relationship between signal to noise ratio and needle insertion angle.

Figures 24A, 24B:
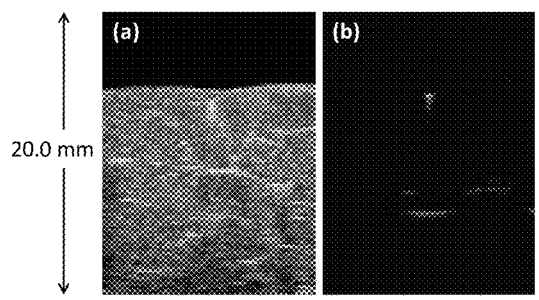

FIGS. 24A-24B show ultrasound and photoacoustic cross-section images of a metal wire inserted horizontally in porcine tissue.

Figure 25:
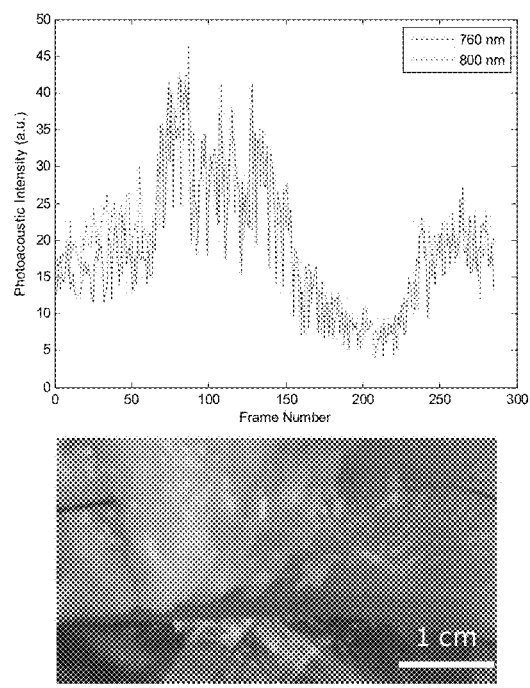

FIG. 25 is a graph depicting the correlation between photoacoustic intensity and tissue position on a tissue sample with varying tissue composition.

Figure 26:
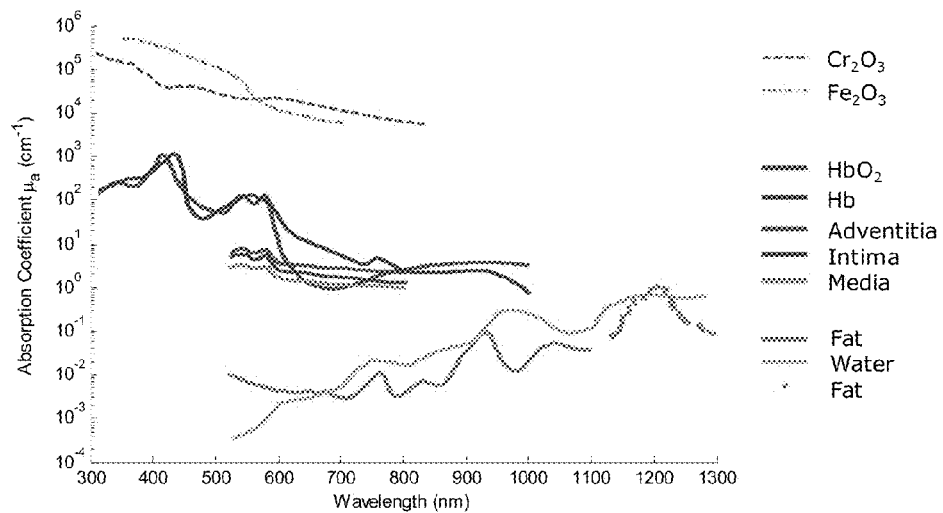

FIG. 26 is a graph depicting the correlation between optical absorption and wavelength for several materials.

Figures 27A, 27B, 27C:
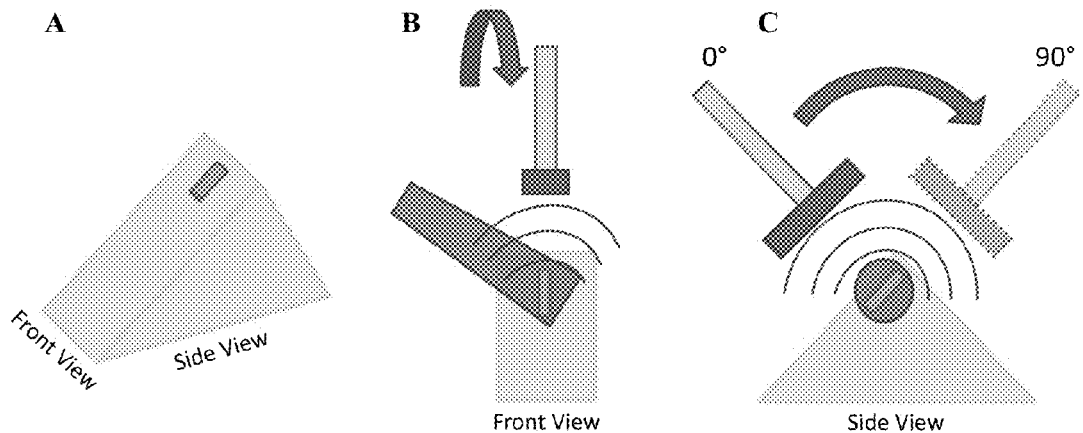

FIGS. 27A-27C show a schematic representation of 3D phantom (A) and front (B) and side (C) view of a transducer rotation apparatus. Yellow triangle/rectangle represents gelatin background; green ellipsoid, seed; blue and gray rectangles, transducer and mount, respectively. Red-shaded regions denote laser irradiation, while black lines represent acoustic transmission, both of which are oversimplifications and included for illustration purposes only. Purple arrow indicates transducer rotation axis.

Figures 28A, 28B:
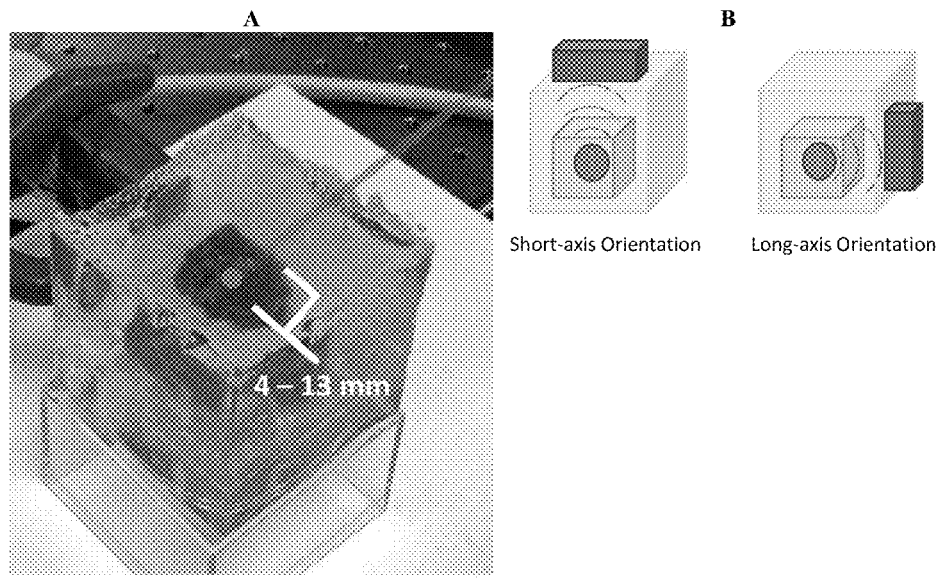

FIGS. 28A-28B depict (A) a picture of a prostate sample cast in gelatin and (B) schematic views of imaging orientations. In FIG. 28A, a green dot denotes approximate placement of seed (long-axis perpendicular to table), a red line indicates example irradiation path, while US transducer is visible in upper-left portion of image (with aperture oriented perpendicular to table). White scale indicates varied distance of seed from front-most sample edge. In FIG. 28B, short- (left) and long-axis (right) orientations are offered. The peach cube depicts the embedded prostate sample.

Figure 29:
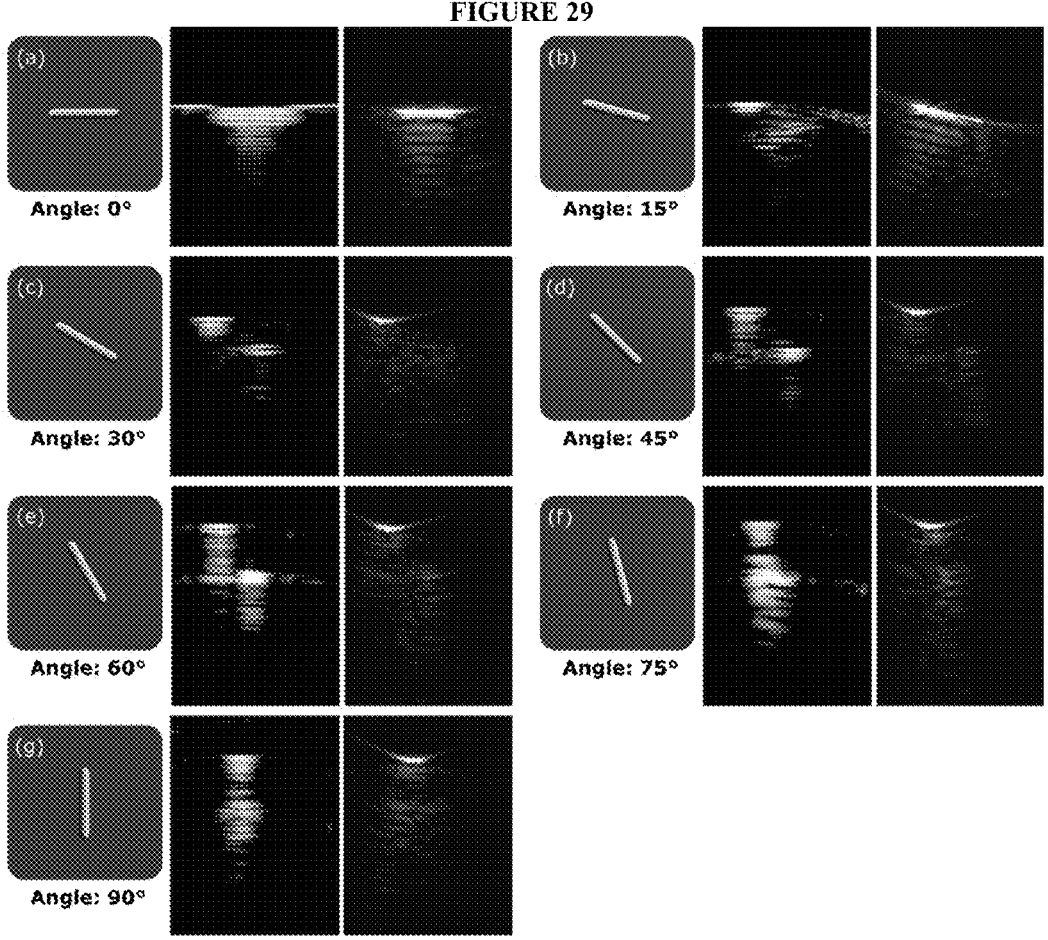

FIG. 29 shows US and PA images of brachytherapy seeds at different rotation angles relative to transducer face. Seed schematics (blue background) denote orientation, while first image immediately right offers US B-mode depiction (grayscale) and second image offers PA imaging depiction (yellow-red colormap). PA and US images are displayed with a 30-dB dynamic range, while all images (including schematic) are presented with same scale (i.e., seed is 0.8×4.5 mm) and co-registered orientations/positions. Transducer face is located/aligned with top margin of schematic.

Figures 30A, 30B:
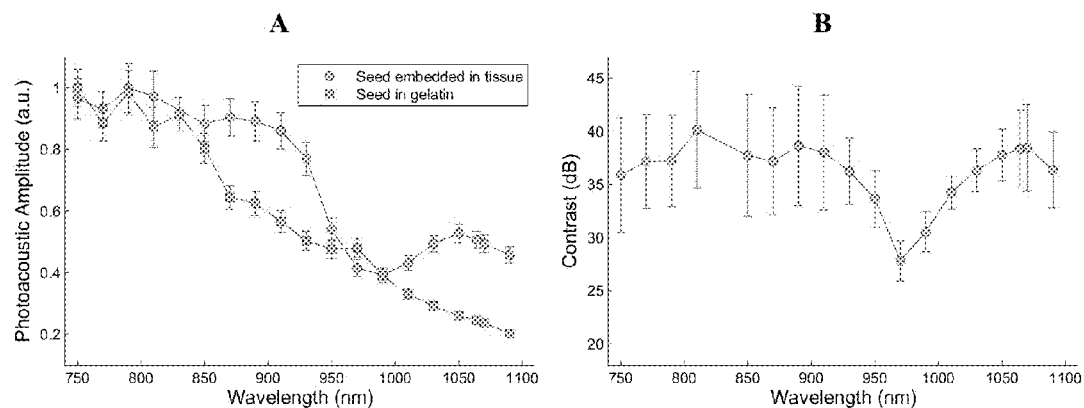

FIGS. 30A-30B are graphs showing: (A) the normalized PA signal of seed embedded in gelatin (square) and embedded in excised bovine prostate (circle) and (B) the contrast spectrum of seed embedded in the prostate sample. Proximal end of seed is embedded approximately 1 mm from prostate tissue surface (in direction of laser source).

Figures 31A, 31B, 31C:
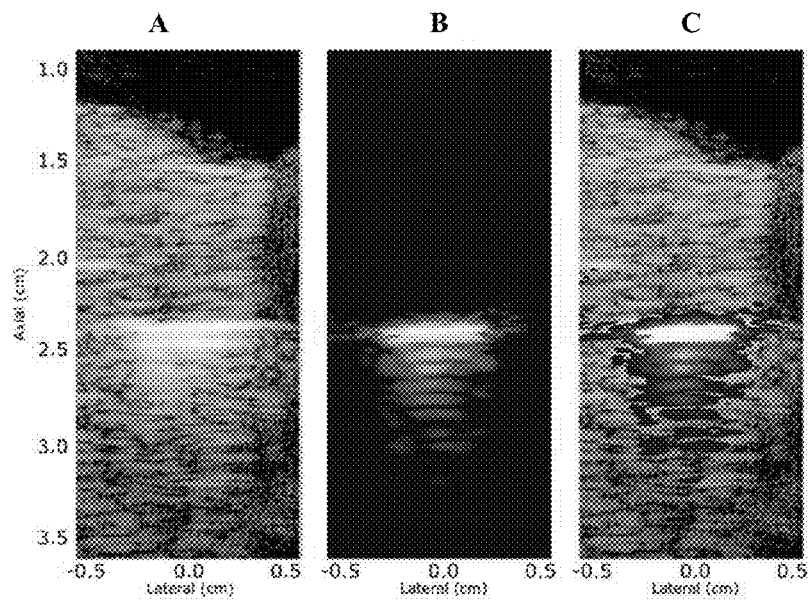

FIGS. 31A-31C show (A) US B-mode, (B) PA, and (C) combined PA/US images of a seed embedded in a bovine prostate sample in the long-axis orientation. PA image was acquired at 870 nm and is displayed with 35-dB dynamic range; B-mode image is displayed with 55-dB range.

FIGS. 32A-32F depict normalized PA spectra and contrast of brachytherapy seed embedded in bovine prostate at three laser irradiation depths: 4 mm (A,D), 10 mm (B,E), and 13 mm (C,F).

Figure 33:
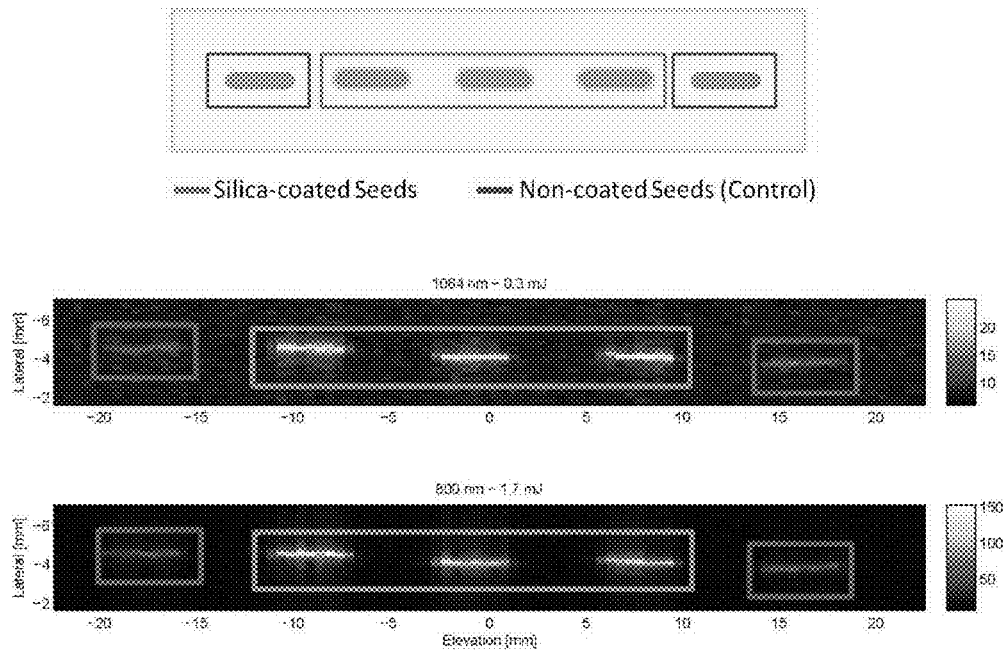

FIG. 33 shows the average PA signal (obtained at 1064 nm (middle) and 800 nm (bottom)) produced by two control seeds (the outer two seeds) and three coated seeds (the inner three seeds).

Figure 34:
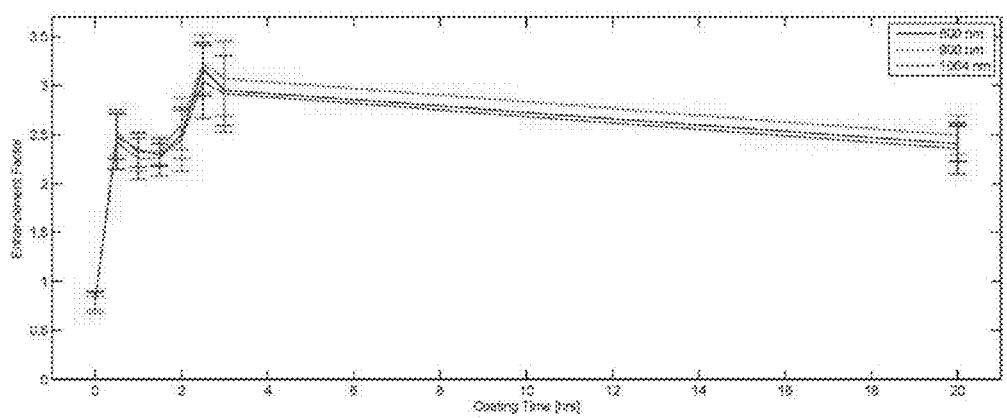

FIG. 34 is a graph showing a quantitative comparison of the results from FIG. 33, which presents average±SD (N=9) signal enhancement as a function of coating time.

Figure 35:
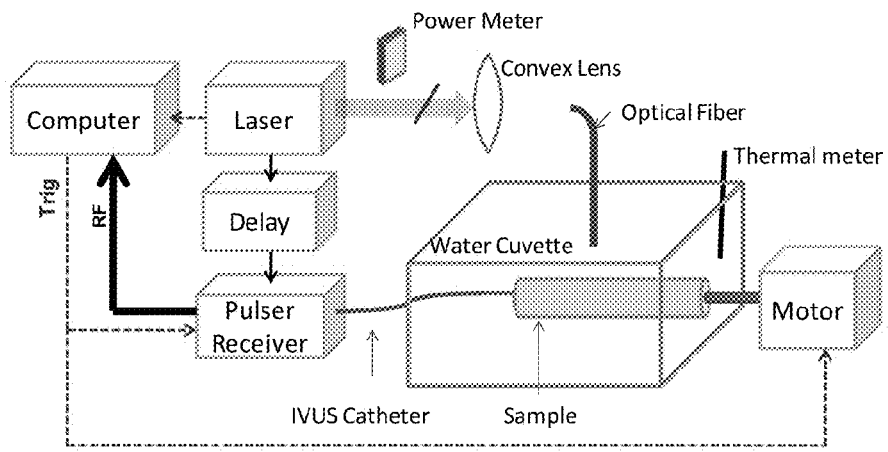

FIG. 35 depicts one embodiment of a combined IVUS/IVPA imaging system for tIVPA imaging.

Figures 36A, 36B, 36C, 36D:
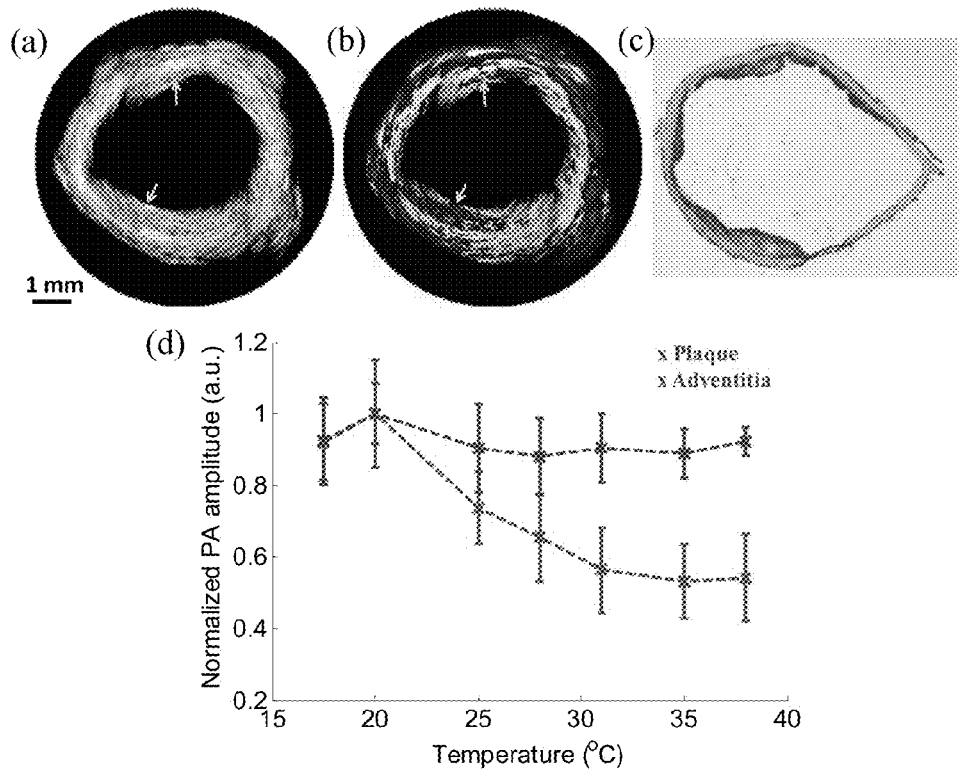

FIGS. 36A-36D show (A) IVUS and (B) combined IVUS/IVPA (1210 nm wavelength) images of the atherosclerotic vessel. The images were acquired at 25° C. Yellow arrows in these images indicate the location of atherosclerotic plaques. FIG. 36C shows that an oil red O stain confirmed that the imaged aorta had lipid-rich plaques. The angular position of the histological slide was chosen based on the visual correlation of the shape of the vessel wall in histology and the IVUS image. FIG. 36D is a graph showing the Comparison of the temperature dependent normalized amplitude of PA signal in plaque and the adventitia (error bars correspond to plus/minus one standard deviation).

Figures 37A, 37B:
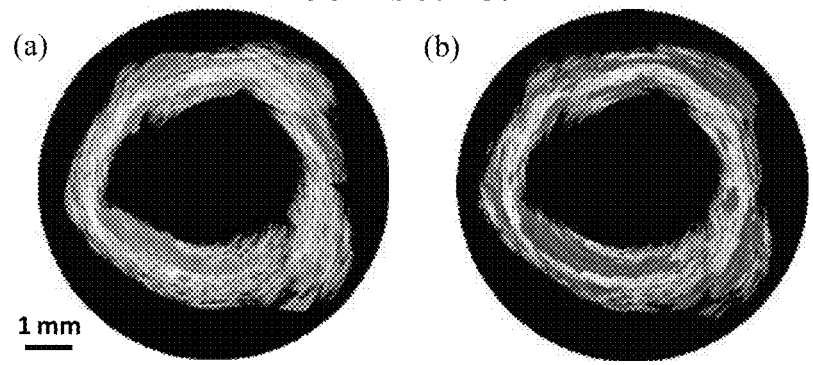

FIGS. 37A-37B show (A) Thermal IVPA (tIVPA) and (B) spectroscopic IVPA (sIVPA) images of the same cross-section of the atherosclerotic artery. Lipid-rich atherosclerotic plaques have similar appearance in tIVPA and sIVPA images while periadventitial fat does not appear in the tIVPA image.

Figure 38:
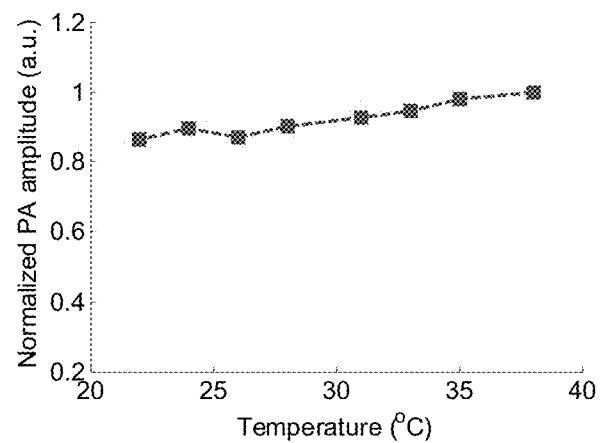

FIG. 38 is a graph showing the temperature dependence of the normalized amplitude of PA signal measured in a sample of rabbit's abdominal fat.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to ultrasound and photoacoustic imaging. More particularly, the present disclosure relates to combined ultrasound and photoacoustic imaging of objects comprising metal.

In some embodiments, the methods of the present disclosure may provide the ability to visualize and/or track temporarily or permanently implanted metal objects. As used herein, the term "metal object" refers to any object which comprises a metal or has an optical absorption coefficient similar to that of metal. Identification of a metal object in the body requires the visualization of landmarks in the body. Ultrasound alone cannot accomplish this due to artifacts, acoustic deflection off of metal surfaces, a low contrast between the metal object and the background, and a low differentiation ability between healthy and diseased tissue. Accordingly, in certain embodiments, the methods of the present disclosure combine both US and PA imaging to offer the high contrast of metal objects in PA imaging with the co-registered imaging of anatomical positioning in US. Used in real time, this combination can offer a very powerful tool not only for identifying metal objects, but also for identifying their relative location to other structures in the body such as tumors and plaques. This ability to identify metal objects and their surroundings is advantageous in image-guided therapy.

In addition, the present disclosure also provides methods utilizing the photoacoustic tracking of a metal object to detect and determine the tissue composition in which the metal object is located. Additional information about tissue composition can be provided to help target the metal object, such as a metal needle, to the region of interest. The signal amplitude from the metal object can signify the type of tissue environment surrounding it, due to the photoacoustic enhancement effect of the Grüneisen coefficient (of the tissue environment) in the photoacoustic pressure equation. As will be further described below, different tissue environments have different Grüneisen coefficients, giving rise to higher or lower photoacoustic signals for absorbers (such as a metal object) inserted into these environments.

Accordingly, in one embodiment, the methods of the present disclosure comprise generating a photoacoustic image of at least a portion of a sample comprising a metal object; generating an ultrasound image of at least the portion of the sample comprising the metal object; and determining the location or positioning of the metal object within the sample by using an overlay of the photoacoustic image and the ultrasound image.

In one embodiment, generating a photoacoustic image of at least a portion of a sample comprising a metal object may comprise exposing at least a portion of the sample to electromagnetic radiation so as to generate an acoustic response, which may then be detected with an acoustic sensor. Based on the detected acoustic response, a corresponding photoacoustic image may be generated of at least the portion of the sample comprising the metal object. By way of brief explanation, the photoacoustic effect results from irradiating at least a portion of the sample with electromagnetic radiation, such as from a pulsed laser beam, to produce a thermoacoustic response. Through the process of optical absorption followed by thermoelastic expansion, broadband acoustic waves are generated within the irradiated sample. An acoustic sensor detects the acoustic waves from the irradiated sample, which is linearly related to the optical absorption coefficient $\mu_a$ and the localized laser fluence. With respect to a metal object embedded within tissue, as metal experiences an optical absorption that is orders of magnitude greater than that experienced by the tissue, the acoustic response from the metal object is higher, relative to the background tissue, thereby providing an image that provides contrast between the metal and the tissue within which it is embedded.

As previously mentioned, in some embodiments, the methods of the present disclosure also comprise generating an ultrasound image of at least a portion of a sample comprising the metal object. In one embodiment, generating an ultrasound image of at least a portion of the sample comprising the metal object may comprise exposing at least a portion of the sample to an acoustic sound wave so as to generate an echo, which may then be detected with an acoustic sensor. Based on the detected echo, a corresponding ultrasound image may be generated of at least the portion of the sample comprising the metal object. By way of brief explanation, ultrasound imaging operates by transmitting an acoustic sound wave, which is then reflected and/or scattered from a sample back to the acoustic sensor. Reconstructed images can provide structural and morphological information based on the acoustic scatterers present in the sample.

In some embodiments, the methods of the present disclosure further comprise determining the location or positioning of a metal object within the sample by using an overlay of a photoacoustic image and an ultrasound image. Accordingly, in these embodiments, the methods of the present disclosure may be particularly advantageous as the high contrast of the metal object obtained in the photoacoustic image may be combined with the anatomical positioning afforded by the ultrasound image so as to identify the location/positioning of a metal object and also its relative location to other structures.

In some embodiments, the methods of the present disclosure may further comprise determining the composition of at least a portion of the sample within which a metal object is embedded. In one embodiment, the composition of the portion of the sample proximate to the metal object may be determined, at least in part, by observing one or more changes in the amplitude of the generated acoustic response object. By way of explanation, the amplitude of the acoustic response can signify the type of tissue environment surrounding the metal object, due to the photoacoustic enhancement effect of the Grüneisen coefficient (of the tissue environment) in the photoacoustic pressure equation shown below in Equation 1. Briefly, the photoacoustic effect may result from irradiating the sample in order to produce a thermal and acoustic response. Light energy that is absorbed in a local region of the sample may be converted into heat, and then may be converted into pressure due to the thermoelastic expansion of the sample. An ultrasound transducer may be used to detect the produced initial pressure, which is linearly related to the optical absorption coefficient of the imaged inclusion, $\mu_a$, the localized laser fluence, $\Phi(z)$, and the Grüneisen coefficient, $\Gamma$, of the surrounding environment, as seen in Equation 1.

$$P_0 \propto \mu_a \cdot \Phi(z) \cdot \Gamma \quad (1)$$

The Grüneisen coefficient is a dimensionless parameter that describes the thermodynamic properties of the tissue environment (Equation 2). The parameter is comprised of $\beta$, the thermoexpansion coefficient, c, speed of sound through the surrounding medium, and $C_p$, the specific heat capacity.

$$\Gamma = \frac{\beta \cdot c^2}{C_p} \quad (2)$$

For stainless steel, the absorption coefficient, $\mu_a$, is 2-3 orders of magnitude greater than optically absorbing tissue constituents in-vivo for a given wavelength of light. Accordingly, different tissue environments have different Grüneisen coefficients, giving rise to higher or lower photoacoustic signals for absorbers (such as a metal object) inserted into these environments. Furthermore, because $\beta$, c, and $C_p$, are all temperature-dependent, tissue-specific parameters, the Grüneisen parameter $\Gamma$ is also temperature-dependent and tissue-specific. Therefore, if the Grüneisen parameter of a specific tissue type at various temperatures is known, photoacoustic imaging can be used to remotely monitor the temperature change. Alternatively, tissue composition may also be identified based on temperature-dependent photoacoustic responses.

As will be recognized by one of skill in the art with the benefit of this disclosure, any suitable source of electromagnetic radiation may be used in the methods of the present disclosure. Examples of suitable sources of electromagnetic radiation may include, but are not limited to, a light source such as a laser, including a tunable pulsed laser or a fixed frequency pulsed laser. In some embodiments, a sample may be exposed to pulses of irradiation with a duration of about 1 nanoseconds ("ns") to about 1000 ns. When the sample to be imaged is simulated by a solid slab tissue, the radiation fluence on the surface of the slab will be about 10 mJ/cm². For other configurations of the test sample, or for living human or non-human bodies the surface fluence will vary, but will always be in a range which is generally considered safe according to the ANSI laser operation standards.

Furthermore, in accordance with the present disclosure, a wavelength of electromagnetic radiation may be chosen, inter alia, to match the type of tissue being image. For example, lipid has an optical absorption peak at approximately 1200 nm. In one particular embodiment, the wavelength of electromagnetic radiation may be in the range of from about 500 to 1200 nanometers. In other embodiments, the wavelength of electromagnetic radiation may be in the range of from about 700 to 1100 nanometers. Similarly, in certain embodiments, more than one wavelength of electromagnetic radiation may be selected. For example, in one particular embodiment, the wavelength of electromagnetic radiation may be of two or more different wavelengths in the range of from about 500 to 1200 nanometers. In other embodiments, the wavelength of electromagnetic radiation may be of two or more different wavelengths in the range of from about 700 to 1100 nanometers. One of ordinary skill in the art with the benefit of this disclosure will be able to select an appropriate wavelength(s) based on the type of tissue sample being evaluated and/or based on other relevant factors.

As previously mentioned, an acoustic response generated by an irradiated sample may be detected by an acoustic sensor. As will be recognized by one of skill in the art with the benefit of this disclosure, any sensor capable of detecting an acoustic response may be used in the methods of the present disclosure. One example of a suitable acoustic sensor may include, but is not limited to, an ultrasonic sensor. Examples of such ultrasonic sensors may include, but are not limited to, transducers including piezoelectric films, such as polyvinylidene fluoride, optical transducers, and optical interferometers.

In certain embodiments, an ultrasonic sensor may also serve as a source of pulsed acoustic sound waves utilized to obtain an ultrasound image of a sample. In such embodiments, a delay switch may be coupled to a synchronous trigger of a laser such that, after or before a photoacoustic image has been acquired, the acoustic detector will itself emit pulsed sound waves. The ultrasonic sensor may then detect echoes of these pulsed sound waves so that the echoes may be utilized to obtain an ultrasound image of the sample.

In some embodiments, a suitable electromagnetic source and a suitable acoustic sensor may be combined into one system, which may also be capable of generating an image based, at least in part, on the detected acoustic responses. Systems suitable for use in the present disclosure may comprise not only a suitable electromagnetic source, and a suitable acoustic sensor, but may also comprise additional electronic and mechanical components such as a pulser/receiver, a digitizer, a motion controller, a three-dimensional positioning stage, a stepper motor, a delay switch, a microprocessor or data acquisition unit, and/or a display monitor. One of ordinary skill in the art, with the benefit of this disclosure, will recognize additional electronic and mechanical components that may be suitable for use in the methods of the present disclosure.

In one embodiment, the methods of the present disclosure may comprise using an intravascular ultrasound (IVUS)/intravascular photoacoustic (IVPA) imaging device, which may be a catheter-based imaging device. An IVUS/IVPA imaging device may be particularly useful when imaging coronary artery stents. Compared to noninvasive cardiovascular imaging modalities such as MRI and CT, combined IVUS/IVPA imaging can achieve higher spatial resolution depending on the transducer frequency used in the application. Furthermore, as compared to invasive but high resolution imaging modalities such as OCT, IVPA has a larger penetration depth of several millimeters relative to 1-2 mm imaging depth in OCT. In addition, by choosing the imaging wavelengths in the near-infrared (NIR) range where the optical absorption of oxygenated and deoxygenated blood is low, IVUS/IVPA imaging may be performed in the presence of luminal blood without the need to flush the vessel with saline.

Samples suitable for use in the methods of the present disclosure may comprise any material that facilitates the propagation of electromagnetic radiation, and also facilitates acoustic wave propagation. In one particular embodiment, the sample may comprise biological tissue. Similarly, the methods of the present disclosure may be used in connection with any type of metal object. Examples of suitable metal objects may include, but are not limited to, a coronary artery stent, a needle, a brachytherapy seed, a surgical staple, an orthopedic implant, a pacemaker wire, etc.

Furthermore, in certain embodiments, the methods of the present disclosure may also be used to image a metal object that comprises a substance that has a strong absorption peak at a specific wavelength. This would enable the metal absorption peaks to be tuned toward or away from wavelengths where a sample shows a strong photoacoustic signal, making the metal object easier to identify alongside other constituents, such as cancerous lesions. These substances, which may be in the form of a coating on the metal object, may also be used concurrently with multi-wavelength photoacoustic imaging to differentiate a metal object from a sample as unique absorption peaks can be expected from the coated metal object. In certain embodiments, the coating may alter a thermodynamic or optical property of the metal object so as to enhance, in relation to a non-coated metal object, the acoustic response generated when the metal object is exposed to electromagnetic radiation. Accordingly, in some embodiments, such a coating may allow for increased detectability of the metal object or for detectability at deeper depths.

Currently, echogenic needle polymer coatings exist that make the needle tip and shaft highly visible under ultrasound. Similar coatings with optically absorbing properties could also be coated onto the metal to make metal implants even more visible at other wavelengths in PA imaging. Various molecularly sensitive coatings could also be used so that the absorption properties of the coated metal would change depending on the tissue background in contact with the metal. These metals could also be used for specific tissue detection. Examples of other suitable coatings may include those comprising silica, gold, metal nanoparticles, and metal nanoparticles coated in silica.

Finally, in certain embodiments, the methods of the present disclosure may also comprise employing a filtering technique so as to at least partially remove or reduce an unwanted echographic pattern, such as a comet tail, from a photoacoustic or ultrasound image. Examples of suitable filtering techniques may include, but are not limited to, a frequency-based filter selected by means of the frequency of the echographic pattern, a wavelet-based filter and a correlation-based filter based off of a multi-wavelength imaging technique.

To facilitate a better understanding of the present invention, the following examples of certain aspects of some embodiments are given. In no way should the following examples be read to limit, or define, the entire scope of the invention.

Example 1

Photoacoustic Imaging of Stents

Materials and Methods

To test the feasibility of a combined intravascular ultrasound (IVUS) and intravascular photoacoustic (IVPA) based method to image stents, imaging studies were performed using 33 mm length, BX Velocity stents (Cordis) deployed in two vessel phantoms mimicking both acoustic and optical scattering properties of tissue. Both phantoms were about 25 mm long with 10 mm outer diameter made of 8% polyvinyl alcohol (PVA). As prepared, PVA is an optically scattering material. For acoustic contrast, 0.1% by weight silica particles of 5 µm size were added to the phantom material to act as ultrasound scatterers.

The first phantom simulated an atherosclerotic vessel with a 3 mm inner diameter. The BX Velocity stent was embedded 1 mm into the inner lumen of the vessel, completely encased within the lumen wall (FIG. 1). Eight millimeters of the stent protruded from one end of the phantom.

The second vessel phantom consisted of three different regions where the stent, relative to the inner lumen, was embedded, deployed (adjacent to the vessel wall), and malapposed (detached from the vessel wall) (FIG. 2). In this phantom, the stent was embedded approximately 1.0 mm within the vessel wall, directly adjacent to the wall, and approximately 1.0 mm malapposed from the vessel wall in the lumen in the different regions, respectively. The malapposed region was formed by separating the stent from the PVA with a plastic mold. Although the stent was separated from the PVA vessel, the stent itself was covered with a thin film of PVA due to the molding process during the phantom preparation.

The laboratory prototype of the IVUS/IVPA imaging setup is shown in FIG. 3. Briefly, a tunable pulsed Nd:YAG pumped optical parametric oscillator laser system (Vibrant B, Opotek, Inc.) was used at 800 nm wavelength to optically illuminate the vessel phantom (FIG. 3A). The photoacoustic signal was detected by a 40 MHz IVUS imaging catheter (2.5 French, Atlantis SR Plus, Boston Scientific, Inc) which was placed within the lumen of the PVA phantom. The laser beam and the IVUS sensing element were first aligned prior to the experiment to ensure detectability of the photoacoustic response from the phantom. In addition to collecting photoacoustic signals, ultrasound pulse-echo signals were also collected using the IVUS imaging catheter connected to an ultrasound pulser/receiver. The cross-sectional IVUS and IVPA images were obtained by rotating the vessel and acquiring 256 photoacoustic/ultrasound A-lines. By longitudinally incrementing the phantom 248 µm each frame, a series of 100 cross-sectional images was collected to reconstruct a three dimensional image of the phantom.

In this ex-vivo prototype imaging setup, external light delivery is unrealistic for in-vivo imaging (FIG. 3B). During an in-vivo IVPA imaging procedure using the integrated IVUS/IVPA imaging catheter, light would be fed into the vessel using a fiber optical delivery system (FIG. 3C) where optical absorption and scattering of blood will diminish the incident laser fluence on the vessel lumen and stent. Therefore, to maximize light penetration at a given fluence and obtain sufficient image contrast, light at 800 nm wavelength was used. At this range, blood is more optically scattering than it is optically absorbing. To mimic this scattering media, milk was substituted for the 30 $cm^{-1}$ scattering coefficient of oxygenated blood at 800 nm. The tip of the optical fiber was placed 5 mm away from the surface of the vessel to simulate the in-vivo IVUS/IVPA imaging where light would travel through blood (scattering environment) before reaching the vessel wall. Therefore, it was conjectured that photoacoustic images of the phantom submersed into milk would be affected by light scattering similar to in-vivo imaging.

Results

The cross-sectional ultrasound image (40 dB display dynamic range) and photoacoustic image (15 dB range) of the first vessel phantom with the stent are shown in FIG. 4. The photoacoustic image shows very high contrast between the stent and the background. Indeed, photoacoustic signal from the stent struts is very strong due to the high optical absorption of metal compared to the vessel which has little to no photoacoustic response. By comparison, the ultrasound image visualizes the complete cross-section of the vessel including the structure and thickness variation of the vessel wall. Since the ultrasound and photoacoustic images are already spatially co-registered, combining the two images shows complementary information. The location of the stent (IVPA image) is given in relation to the vessel (IVUS image). Quantitatively, the radial distance from individual struts to the lumen wall, measured from the IVUS/IVPA image, varied between 0.7 to 1.2 mm. These measurements are in agreement with the design of the phantom—the phantom mold was milled to separate the lumen wall from the stent by approximately 1.0 mm.

To visualize the entire vessel wall and the stent, a three-dimensional (3D) image of the phantom was produced (FIG. 5). To visualize the structure of the stent in the context of the structure of the phantom, the transparency of the ultrasound image was modified such that the photoacoustic signal can be seen, showing the structure of the stent.

The intravascular ultrasound, photoacoustic and combined IVUS/IVPA images of the second vessel phantom are shown in FIG. 6. By imaging at various locations along the length of the vessel, the distance between the stent and the lumen wall was assessed. In the region of the embedded stent (FIG. 6A), the distance of the stent struts to the lumen wall was measured to range from 0.7 to 1.0 mm. In the region where the stent was merely adjacent to the vessel wall (FIG. 6B), the image visualized the correct position of the stent struts relative to the vessel wall. Finally, in the malapposed region (FIG. 6C) the stent struts were measured to be 0.8 to 1.1 mm away from the wall. The position of the stent struts varied due to preparation of the PVA phantom mold. However, the diameter of the stent was measured to be a constant 5.0 mm throughout the entire stent, in agreement with the specification set out by the manufacturer. Due to the molding process used in fabricating the malapposed section (FIG. 6C), a thin layer of PVA was formed on the surface of the stent. The presence of this PVA film explains the additional inner ring where the stent is located. Nevertheless, IVPA imaging was unaffected. The images in FIG. 6C demonstrate that far more complex geometries and positioning of stents within the vessel can be imaged using IVUS/IVPA imaging.

Figures 7A, 7B, 7C, 7D:
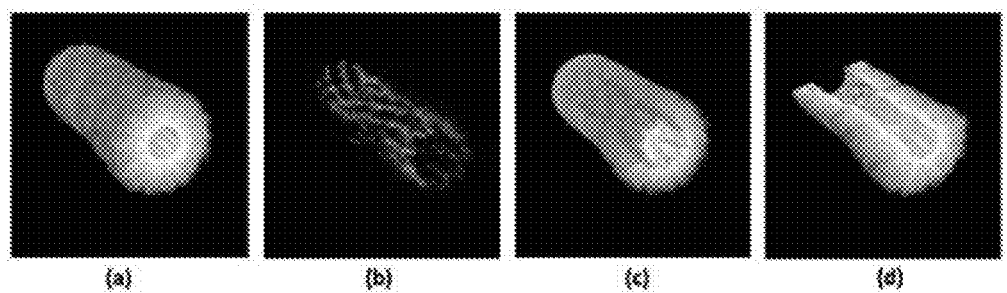

Similar to the first phantom, a set of 80 cross-sectional images were combined to produce a 3D image of the vessel and stent (FIG. 7). By displaying the cut-away of the 3D reconstruction, the shape and position of the stent within the vessel is easily assessed (FIG. 7D). Again, the photoacoustic image was able to visualize the stent (FIG. 7B) and to correctly measure the inner diameter of the stent to be exactly 5.0 mm, the reported diameter for the stent. Furthermore, the stent could be visualized in the context of the vessel geometry (FIG. 7C) to identify the regions of embedded, deployed, and malapposed stent (FIG. 7D).

The experiments were also performed to identify the influence of luminal blood on the quality of photoacoustic imaging. The comparison between the blood-simulating environment and the water environment showed virtually no difference in either the ultrasound or photoacoustic images (FIG. 8). As expected, photoacoustic signal intensity showed a small reduction in the peak signal intensity from the stent due to the optical scattering properties of the milk. Nevertheless, image quality was not significantly reduced—the stent within the vessel wall was clearly visualized in both images.

Discussion

The combined IVUS and IVPA imaging system was able to image several millimeters deep which is necessary for the intravascular imaging of coronary arteries. The high-frequency 40 MHz IVUS catheter allowed for an axial resolution of several tens of micrometers in both IVUS and IVPA images. The resolution of IVUS/IVPA imaging is slightly worse compared to OCT imaging, but the larger imaging depth allowed for complete viewing of the 10 mm diameter vessel. Furthermore, the full structure of the phantom is visible, unobscured behind the stent struts, thus allowing the position of the stent within the vessel wall to be visible, whether or not the stent was hidden from view.

Overall, the diameter of the stent was correctly measured throughout the stent according to the specification set out by the manufacturer. An in-vivo environment can cause implanted stents to be crushed or deformed which can lead to problems such as thrombosis or stent drift. Photoacoustic imaging allows for accurate assessment of not only the size of the stent but also the stent shape in relation to the implanted environment.

The stent struts were always fully visible in the photoacoustic image, but at best only partially visible in the ultrasound images. In these regions visible in ultrasound, the phantom background is hypoechoic and therefore the stent appears in the ultrasound image with sufficient contrast against this background. In the phantoms used in this example, silica particles were added to provide acoustic scattering. Regions that did not contain uniformly mixed silica particles appeared hypoechoic under ultrasound. However, under conditions where the local background regions were highly acoustically scattering, the stent was difficult to visualize under ultrasound alone. Even in the malapposed region of the phantom (FIG. 6C) where traces of the stent struts can be seen, the presence of the PVA film reduced the ability to locate the struts using ultrasound alone. In the photoacoustic image, conversely, the contrast is determined by optical absorption. Since metal struts of the stent are strong light absorbers, the photoacoustic image revealed the precise location of the metal struts.

Since IVPA imaging is based on the same hardware as IVUS, it is understandable that photoacoustic imaging of stents may be susceptible to similar artifacts seen in IVUS. These include artifacts due to off-centered positioning of the transducer within the lumen and acoustic reverberation artifacts within the metal stent implant. IVPA can also bring its own issues, including light delivery through tissue or through other optically attenuating materials.

The optical attenuation of light in blood should not detrimentally affect imaging of stents in-vivo. In this example, the optic fiber was placed at a greater distance from the vessel surface than it would be from the inner boundary of the vessel wall in in-vivo imaging. In other words, in in-vivo experiments the light would travel a smaller distance and be attenuated less. Therefore, the resulting images in-vivo should be able to assess stent viability. Furthermore, laser pulse energies in this example, measured at the fiber output, were approximately 1.75 mJ. Due to the high optical absorption properties of metals, the energy used to obtain a photoacoustic response can be decreased. For IVPA imaging in real-time, necessary in the clinical environment, lower energies may be required to increase the laser pulse repetition rates. For these applications, a tunable OPO laser system may not be a suitable choice. However, pulsed Nd:YAG lasers operating at 1064 nm could be considered as these lasers can have pulse repetition rates from 1 to 10 kHz. While the pulse energy of these lasers is only upwards of 100 µJ, fluences similar to this example could be obtained by decreasing the fiber size or focusing the laser beam to a smaller diameter. It should be noted that smaller fiber sizes will undoubtedly be required in a clinical IVUS/IVPA system in order to meet lumen clearance diameters for the combined imaging catheter containing the IVUS transducer and IVPA optical fiber.

This example shows that IVUS/IVPA is a promising modality to image stents in vivo.

Example 2

Photoacoustic Imaging of Metal Needles in Tissue

Experiments were performed using common commercially available clinical metal needles inserted into tissue and tissue-mimicking phantoms. The presence of these clinical needles was detected using combined US and PA imaging. In each experiment, the acquired PA images outlined the presence of the metal implant, and the US image provided information about the surrounding structure. During postprocessing, the comet tail artifacts were reduced using a filtering approach, thus enabling the previously distracted background in PA imaging to be better visualized. The combined US and PA imaging enabled accurate measurements of the needle's position within the tissue. The accuracy of these measurements demonstrates the usefulness of PA imaging in visualizing metal needles and other metal implants in vivo.

Materials and Methods

To test the feasibility of US and PA to image metal needles in tissue, imaging studies were conducted using different sizes of needles. In the first experiment, a Cortex ultrasound imaging system (Winprobe Corporation, North Palm Beach, Fla.) was used for rf data acquisition (FIG. 9). This US system was interfaced with a 7-MHz center frequency, 14-mm-wide, 128-element linear array transducer to image the needles. An Nd:YAG pump laser output (Vibrant B, Opotek, Inc., Carlsbad, Calif.) at 1064 nm was used to optically illuminate the tissue phantom. Laser fluence in all experiments was measured to be approximately 10 mJcm$^2$. Laser light was delivered through an 18-fiber optical bundle fixed around the transducer, and the needle sample was placed in the imaging plane of the US imaging transducer (FIG. 9). This arrangement enabled both light and sound delivery along the same plane. Each fiber in the bundle was 0.6 mm in diameter with a numerical aperture (NA) of 0.22. Fiber bundle efficiency was approximately 60%. In this example, a 30-gauge (30 G)×1.0-in. hypodermic syringe needle (FIG. 10), made of 305 bulk stainless steel (Becton Dickinson, Franklin Lakes, N.J.) was inserted horizontally into a fresh healthy porcine muscle specimen. The approximately 30×30×30 mm$^3$ tissue sample was immersed in water for acoustic coupling between the US transducer and the tissue (FIG. 9). US and PA rf signals were collected with the needle oriented orthogonal to the imaging plane, then the transducer was axially rotated 90 deg, and the imaging procedure repeated, capturing the length of the needle in the imaging plane.

To investigate the angular dependence of the US and PA signal, a second experiment was performed using a 7.5-MHz, f/4, single-element transducer, mechanically scanned across the axial dimension of a set of needles using both US and PA imaging (FIG. 11). The purpose of this experiment was to determine the needle angles at which the metal needle would be visible, both in US and PA imaging and to demonstrate the effectiveness of PA imaging for detecting needles which are more often than not inserted angled from the transducer. Five 21 G×1.0 in. needles made of 305 bulk stainless steel (Becton Dickinson, Franklin Lakes, N.J.) were positioned both in water and in gelatin phantoms at angles of 0, 5, 10, 20, and 30 deg relative to the horizontal plane, i.e., the surface of the US transducer. The gelatin phantom was created using 6% gelatin by weight, and a small amount (less than 1%) of 40-µm-size silica particles, which served as optical scatterers. PA imaging was conducted at 800 nm and light was delivered using a single optical fiber. The fiber had a diameter of 1.5 mm and an NA of 0.39.

Results

In the first experiment, the metal needle, in porcine tissue, was inserted parallel to the transducer surface and perpendicular to the imaging plane. Cross-sectional US and PA images of the needle and tissue were produced (FIGS. 12A and 12B). The US image (FIG. 12A) shows a bright signal in the middle of the image where the needle is located. Surrounding the needle's signal is the US speckle obtained from the porcine tissue. The PA image at the same position also showed a bright signal in the center corresponding to the needle cross section. After obtaining these images, the sample was rotated 90 deg relative to the transducer, aligning the needle shaft directly in the imaging plane of the transducer (FIGS. 12C and 12D). Similarly, the US image (FIG. 12C) displays a bright acoustic reflection from the needle, surrounded by acoustic speckle from the tissue background. The PA image of the needle shaft (FIG. 12D) also produced a large signal from the needle, but very little signal from the background, similar to the PA image in (FIG. 12B). As the metal needle was placed parallel to the transducer surface in these images, the needle was easily visible in the US and PA images. At this orientation (i.e., a perpendicular angle between the axis of the US beam and longitudinal axis of the needle), the needle produced a strong US signal due to the high specular reflectivity of the needle. US comet-tail artifacts were also created behind the needle since acoustic waves were reflected within the needle, creating additional signals that appeared to propagate beyond and around the needle. The artifacts introduced into the US image, subsequently reduced the ability to determine the precise location of the needle. However, the comet tail made it very easy for the needle's presence to be identified in the image. The PA signals here also confirmed the presence of the highly absorbing metal needle. US and PA images (FIG. 13) were also obtained with the needle inserted into the phantom at a slight downward angle. In these images, the cross section of the needle was once again located in the center of the images, similar to FIGS. 12A and 12B. However, the needle here was angled away from the transducer. The US image still showed the background speckle of the porcine tissue, but the needle in the center of the image could not be easily visualized (FIG. 13A). A PA image was also obtained at the same position (FIG. 13B). Despite the angled needle being invisible in the US image, the PA image still showed a bright spot in the center of the image where the cross section of the needle was located. By combining FIGS. 13A and 13B, the coregistered US and PA images displayed the presence of the angled needle in the tissue background (FIG. 13C).

In the US image, the angled needle reflected the acoustic pulses away from the transducer, thereby decreasing the signal intensity from the needle, resulting in decreased visibility in the resulting image. However, the PA signal was not significantly affected by this angular dependence and the needle remained highly visible within the tissue background even when it was not perpendicular to the transducer. In general, the PA response from rounded objects occurs omnidirectionally, which enables the signal to be less affected by the needle angle compared to the US image. Comet-tail artifacts are, however, directionally dependent, which is why they are not visible in the image of an angled needle. Furthermore and more importantly, there is excellent contrast in the PA response between the needle and the background tissue.

In the second experiment, cross-sectional US and PA images of the five angled 21 G needles were obtained (FIGS. 14A-14B). From left to right, the needles were inserted into an acrylic holder at decreasing angles from 30 to 0 deg. The US image (FIG. 14A) shows the cross sections of the needle with decreasing visibility as the needle angle was increased. Similarly, the PA image (FIG. 14B) shows the needles at the same position but with less decrease in signal as needle angle was increased. The addition of the gelatin phantom background in FIGS. 15A-15B show both the US and PA images of the needles, similar to FIGS. 14A and 14B. The US image of the needles in the gelatin phantom shows overall decreased visibility of the needles in the presence of the background speckle (FIG. 15A). On the other hand, all the needles were fully visible in the PA image (FIG. 15B); the PA signal intensity did not decline with needle orientation at the angles used in this experiment. Furthermore, the presence of optical scatterers helped to deliver light within the phantom. FIG. 15B shows increased PA signal due to better light delivery to the needles in the phantom.

In both the water (FIG. 14) and the tissue-mimicking phantom (FIG. 15) experiments, the maximum signal intensity came from the needles that were horizontal from the transducer surface. In water, all the needles were at least dimly visible in the US image, although the signal intensity and spatial resolution was severely limited at needles angled greater than 10 deg. The addition of acoustic scatterers in the phantom background made the needles less visible under US. Needles at angles greater than 10 deg were invisible against the background. The PA signals from the needles remained easily visible in the gelatin, except for a slight decrease in signal intensity due to light attenuation from the phantom. This did not adversely affect the imaging of the needles, as they were still very visible due to the high absorption coefficient of metal.

Discussion and Conclusions

US and PA images of needles are shown in FIGS. 12-15. In each set of images, the PA images showed very high contrast between the metal and the phantom or tissue backgrounds. Indeed, the PA signal from the metal is very strong due to the high optical absorption of metal compared to the gelatin phantom, which has little to no PA response and therefore results in very high contrast. In tissue, high contrast between the metal structure and tissue constituents was also found. Optical absorption of other tissue constituents is generally known to be far lower than that from the metal in the near-IR spectrum range. By comparison, the US image visualized the tissue structure and morphological features. Since the US and PA images were already spatially coregistered, combining the two images showed complementary information. The locations of the metal implants (PA image) were given in relation to the background tissue (US image).

Both experiments showed strong comet-tail artifacts when imaged with US and PA imaging. Fast Fourier transforms (FFTs) of the a-lines containing rf signals showed that the frequency content of the comet tail was slightly different than the center frequency of the transducer. Therefore, bandpass filtering was performed to reduce the artifacts from the PA image of the needle in FIG. 12. Prior to applying the signal filter, comet-tail artifacts could be seen emanating from the position of the needle in the PA image (FIG. 16A). When correct bandpass filtering was performed (4 to 10 MHz), the comet tail disappeared from the image (FIG. 16C). However, specifying the incorrect frequency range (3 to 10 MHz) resulted in an undesired treatment of the image and did not correctly remove the image artifacts (FIG. 16B).

Bandpass filtering was able to remove the image artifacts, albeit at a decrease in the contrast-to-noise ratio (CNR). Without filtering, the CNR of FIG. 16A was found to be 39.3 dB. FIG. 16B was reported to contain a CNR of 38.2 dB, and FIG. 16C had a CNR of 32.5 dB.

Attempts to perform the same filtering technique to the US image were unsuccessful. Examination of the time domain signal revealed that the comet-tail artifact produced in the US image contained a discontinuous signal different from the PA image. While the resulting artifacts in the US and PA signals were visually similar, the PA comet-tail signal was continuous, decreasing over time, similar to an acoustic reverberation (FIG. 17A). On the other hand, the US comet tail was discontinuous, having burst-like signals that decreased in amplitude over time (FIG. 17B). These burst-like signals in the US image are therefore not easily removed without using more advanced filtering methods.

The combined US and PA imaging modality was able to image 1 to 2 cm into tissue, the depth necessary for the imaging of metal needles inserted into the body. The current practice of using US imaging for guidance is ineffective to image metal in all cases, especially where highly reflective surfaces redirect US echoes away from the transducer. In most cases, clinicians are only able to use the US shadows from the metal to infer the location of the needle. The experimental results presented here demonstrate that PA imaging is suitable for imaging metal. Combined with US imaging, the PA signal from the metal inclusions was visible in relation to its position to the surrounding tissue/phantom structures, which were visible in the US signal.

The use of 1064-nm-wavelength light is a huge advantage for clinical in vivo settings due to the low cost and simplicity of the Nd:YAG laser, deep penetration of the light into tissue, and high PA contrast between metal objects and surrounding tissue. By using a 1064-nm laser, users do not require an expensive, complex laser system to conduct imaging tests. At a 1064-nm wavelength, light offers deep penetration into tissue and therefore imaging will require less laser fluence for the PA signal, while still preserving SNR, CNR, and safety. The imaging studies conducted here used laser energies well below the maximum permissible exposure level set by the ANSI standard. These laser energies coupled with an array-based imaging transducer make it possible to image PA signals in real time. The setup in this example was limited to a repetition rate of 10 Hz, but inexpensive lasers operating at 30 Hz or higher could be used for real-time imaging. The PA contrast in the tissue studies demonstrated that at 1064 nm, metal was more highly absorbing than the surrounding tissue, therefore showing that 1064 nm is an effective wavelength choice for imaging metal in the body.

Though the first PA imaging example was conducted at 1064 nm, the second experiment was conducted at 800 nm, suggesting that multiple wavelengths could be used for spectroscopic PA imaging, which could be utilized to further differentiate between metal and tissue. Since the PA effect is directly related to optical absorption, PA data from multiple wavelengths could be used to calculate absorption spectra in the resulting image. Tissue constituents, having a unique optical absorption spectrum from metal, could then be differentiated from the metal, identifying the composition of tissue with respect to the location of metal implants.

The previous example 1 showed that PA imaging of metal in the body is not limited to needles. A host of metal devices are used in the human body, either temporarily or permanently, many of which must be identified or monitored. As discussed in Example 1, combined intravascular US (IVUS) and PA imaging (IVPA) has been shown to image arterial stents and their positioning within the arterial wall. The combination of IVUS and IVPA was found to give complementary information as the US image gave structural/morphological information of the arterial wall, while the IVPA image could hypothetically show the location of the stent, its position within the wall, and also the location of arterial plaques.

It has also been proposed that this combined US and PA imaging could be used to image brachytherapy seeds during and after implantation into the body. Brachytherapy seeds are implanted to locally treat prostate cancer. However, the seeds have been found to migrate throughout the body, which can cause problems as they lodge themselves in other areas of the body such as the lungs. PA imaging could be used to detect the location of the seeds as they shift around in the prostate. The imaging could be performed tomographically, reconstructing multiple slices of US and PA data to create a 3-D image of a localized region.

Example 3

Photoacoustic Imaging of Stents

Materials and Methods

An experiment was conducted to test the imaging and detection of a stent ex-vivo. An excised aorta from a rabbit model of atherosclerosis was used. In particular, a New Zealand white rabbit was kept under a low 0.2% cholesterol diet for 12 months. Rabbits under these dietary situations can develop severe atherosclerotic lesions in the aorta. The rabbit was sacrificed and the aorta was excised. A 4.5 mm inner diameter BX Velocity™ stent (Cordis) was deployed into the excised aorta according to the manufacturer recommended pressure rating. The stent was inflated to a pressure of approximately 12-14 atm, which resulted in an inflated diameter of approximately 4.64-4.76 mm. Combined US and PA imaging was performed with a custom designed integrated catheter inserted into the lumen of the excised artery in a water tank. Spectroscopic PA imaging was performed from 650-710 nm and from 750-900 nm, in increments of 10 nm. Laser fluence was measured at each pulse and used to normalize the PA signal in post-processing.

Images were processed using custom Matlab code written to process and display the scan-converted IVUS/IVPA images. For quantitative analysis, the PA signal was taken from a small kernel corresponding to an area where one stent strut located, and confirmed based on the B-mode image. Data within this kernel was averaged to obtain a signal value for the center pixel. Data values were recorded across all wavelengths to obtain a rough optical spectrum from 650 to 900 nm. This spectrum was then correlated to all other pixels in the image, taking into account the PA data obtained across all the wavelengths. Correlation values for each pixel were then overlaid in an image over the original PA image.

Results

Images were acquired from the experiment using a combined IVUS/IVPA catheter to image a stent deployed in an excised rabbit aorta (FIGS. 18A-18C). Similar to the phantom studies presented in Example 1, the stent struts appeared with high contrast in the PA images (FIG. 18B). The combined US and PA image (FIG. 18C) showed good co-registration regarding the presence and location of the stent struts for half of the cross-section. The stent struts in the image from the 6 o'clock to 11 o'clock position were less visible in the image, but the comet-tail artifacts from each stent strut could still be seen.

Spectroscopic analysis was also able to identify the presence of the stent based on the unique multi-wavelength PA signal of the metal (FIGS. 19A-19B). The location of the stent struts as seen in the PA images showed good correlation with the spectrum of the original selected kernel. Each pixel was displayed according to a color bar (FIG. 19A), with high correlation pixels displayed in red, and low correlation in blue. It was observed that the comet-tail artifacts that appeared distal to each stent strut did not correlate well with the original kernel. Finally, pixels that showed a correlation coefficient greater than 80% were overlaid on the US image (FIG. 19B).

Discussion

From the ex-vivo tissue images, the stent struts were highly visible in the PA images. Each strut from the 12 o'clock to 6 o'clock position produced a strong PA signal, but also a trailing comet-tail artifact similar to those seen in needles (Ziskin, M. C. et al. J Ultrasound Med, (1982). Su, J. L., et al. J. Biomed Opt., (2010)). Spectroscopic PA imaging demonstrated the ability to isolate the signal from the metal stent strut from its associated comet-tail artifact. This procedure shows that the amplitude of the comet-tail artifact produced is not linearly proportional to the optical absorption of metal. Multi-wavelength PA imaging could possibly be used as a process to filter out the comet-tail artifact, therefore isolating only the PA signal from the stent strut.

However, the absence of strong PA signals from the 6 o'clock to 11 o'clock positions in FIG. 18B, highlight an instrumentation issue rather than a fundamental limitation. For the combined IVUS/IVPA catheter used here, the optical and acoustic beams were only overlapped at a certain imaging depth, due to the construction of the catheter.

Example 4

Determining the Composition of Tissue Surrounding a Metal Needle Using Photoacoustic Imaging Materials and Methods To test the hypothesis that ultrasound and photoacoustic imaging is well suited for imaging needles, and also for detecting the surrounding tissue composition, a set of ex-vivo experiments was performed on healthy porcine tissue. In the first experiment, an 18-gauge needle (Becton Dickinson, Franklin Lakes, N.J.) was also inserted into healthy porcine tissue horizontal and angled relative to the imaging transducer, and then imaged with the VEVO 2100 dual ultrasound/photoacoustic imaging system (VisualSonics Inc. Toronto, Canada) using a 21-MHz center frequency, 256-element, array transducer. A standard 21-gauge needle (Becton Dickinson, Franklin Lakes, N.J.) was also inserted into healthy porcine tissue at angles 0°, 5° and 10° relative to horizontal, and imaged with a 7.5 MHz center frequency, 128-element array transducer (Winprobe Corporation, North Palm Beach, Fla.). Photoacoustic imaging was performed with a tunable Nd:YAG pulsed laser (Spectra-Physics, Mountain View, Calif.) operating at 800 nm. Light was delivered using a fiber bundle that focused the light at approximately 2 cm from the ultrasound transducer surface. The transducer was placed on the surface of the porcine tissue. Ultrasound gel was used for acoustic coupling between the transducer and the tissue. Images were collected with the needle in both longitudinal and transverse orientations. The resulting ultrasound and photoacoustic images demonstrate the high visibility of the needles using the photoacoustic modality.

To test whether the photoacoustic signal could differentiate the tissue environment, a second experiment was performed. Healthy porcine tissue with distinct fat and muscle regions along the surface of the tissue was used. A 316L stainless steel wire, to mimic a fine needle (approximately 0.4 mm in diameter), was inserted superficially along the surface of the tissue so that the muscle and fat regions were intersected along the length of the wire. FIG. 20 is a photograph of the metal wire inserted through the fat and muscle regions of the porcine tissue. The wire was inserted superficially through the surface of the tissue in order to reduce the effect of light extinction passing through the tissue in photoacoustic imaging.

At any given region, the wire was only 1-2 mm deep inside the tissue. The shallow depth of the wire was chosen so that light attenuation through the tissue would not significantly affect the laser fluence irradiating the stainless steel wire. The same 21-MHz transducer was also used here. An imaging pullback was performed in order for a three-dimensional image to be reconstructed of the tissue and wire. Images were normalized by laser fluence in post-processing, and the photoacoustic intensity of the wire was plotted in relation to position in the tissue.

Figures 21A, 21B, 21C, 21D:
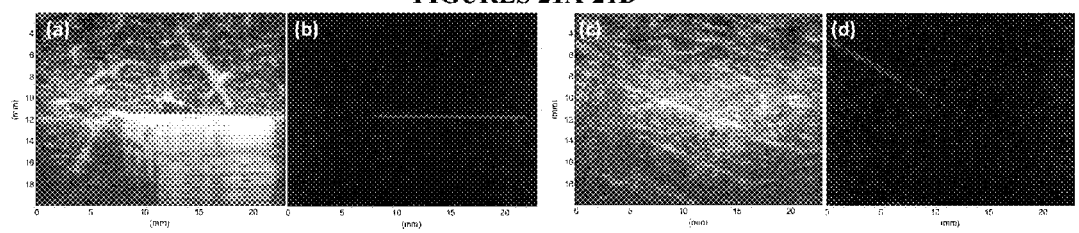

FIGS. 21A and 21B show the combined ultrasound and photoacoustic images show the wire inserted longitudinally into tissue. When the wire was oriented horizontally with respect to the transducer head, both ultrasound and photoacoustic imaging are well-suited for imaging due to the high specular reflectivity in ultrasound, and high optical absorption in metal for photoacoustic imaging. However, when the insertion angle of the wire is slightly angled with respect to the transducer head, the wire is rendered invisible in the ultrasound image, as shown in FIG. 21C. However, as shown in FIG. 21D, the photoacoustic image continues to expose the presence of the wire.

Signal degradation due to an increasing insertion angle is shown in FIGS. 22A-22C. FIG. 22A depicts 0°, FIG. 22B depicts 5°, and FIG. 22C depicts 10°. As can be seen in FIG. 22C, at 10° the wire is invisible in the ultrasound image. As the insertion angle increases, the signal ratio between the wire and the background decreases in both ultrasound and photoacoustic. However, the signal drops much more dramatically in the ultrasound. The contrast between the wire and the background is very low at insertion angles greater than 10°. The signal loss in photoacoustic imaging is not as troublesome. The signal amplitude is less affected by wire angle, and the lack of background signal in the photoacoustic image results in a higher signal-to-noise ratio when it comes to identifying the position of the wire, as demonstrated in FIG. 23. Lack of background signal would not always be applicable as tissue constituents do have optical absorption, though absorption of metal is typically several orders larger.

As can be seen in FIG. 23, signal to background ratio as a function of wire insertion. In the photoacoustic image, wire to background signal always remains higher than the corresponding ultrasound image. At 10° where the wire is invisible, as shown in FIG. 22C, the signal-to-background ratio is very low.

The photoacoustic signal from the wire study suggests that photoacoustic signals are significantly dependent on the surrounding tissue environment. The ultrasound and photoacoustic images correlate nicely. Since the wire is oriented horizontally with respect to the ultrasound transducer, the wire appears in both the ultrasound and photoacoustic images, as depicted in FIG. 24. Despite showing some photoacoustic image artifacts, the only signal in the image is from the metal wires itself, as shown in FIG. 24B. When the amplitude of the wires' photoacoustic signal is compared to tissue position the change in amplitude correlates well with the presence of fat or muscle in the tissue sample. As can be seen in FIG. 25, data plots show that the photoacoustic amplitude is higher for the wire located in the fat region than in the muscle region. From a qualitative point of view, the data suggest a higher signal from the metal wire when inserted into fat than muscle. The amount of signal enhancement correlates well with the difference in Grüneisen coefficients between pork fat and pork muscle which suggests an enhancement of approximately 400%.

Photoacoustic imaging in FIGS. 21 and 22 showed very high contrast between the wire and the porcine tissue background. The high contrast found in these images was due to the high absorption coefficient of metal compared to the porcine tissue which has little to no photoacoustic response. By comparison, the corresponding ultrasound image was able to visualize the background morphology of the tissue. Co-registering the two images allows complementary information to be known. That is, the location of the metal is known in relation to the background tissue.

Both the ultrasound and photoacoustic image modalities could detect needles that were oriented horizontal to the transducer surface. Specular acoustic reflections off of the metal's surface restricted ultrasound's ability to detect needles that were angled more than 10-15° away from the transducer. This specular reflection phenomenon did not affect photoacoustic imaging as much, as photoacoustic signals are produced omni-directionally from the surface of irradiation by the laser. In so doing, photoacoustic signals from the metal surface can be more easily detected than reflected ultrasound pulses.

The effect of tissue environment on photoacoustic amplitude was demonstrated by the change in signal amplitude due to the metal's location in different tissue environment. While the results match qualitatively with the enhancement due to the Grüneisen coefficients, the mechanism by which this enhancement occurs is not yet quite understood. It is hypothesized that the effect is due to the interfacial thermal resistance between the surface of the bulk metal and the surrounding environment.

While energy fluence was accounted for in the experimental trials, it is possible that light scattering and absorption would play a role in increasing or decreasing the amount of energy incident upon the metal to generate the photoacoustic effect. However, by inserting the metal wire at a very shallow superficial depth below the tissue surface, the optical extinction due to tissue was diminished.

FIG. 26 compares the optical absorption ($\mu_a$) of stainless steel constituents ($Cr_2O_3$ and $Fe_2O_2$) to the optical absorption of tissue constituents. As can be seen in FIG. 26, metal absorption ($cm^{-1}$) is up to 3-4 orders of magnitude higher than strongly absorbing tissue. The higher $\mu_a$ values result in a higher PA signal. The Grüneisen coefficient of the surrounding environment can also directly affect the resultant photoacoustic signal amplitude. Various tissue have unique Grüneisen coefficients which may allow comparison of tissue composition through photoacoustic signal amplitude. (e.g., porcine fat is approximately 400% higher than porcine muscle.)

The present example demonstrates the increased utility of using photoacoustic imaging for the tracking of needles in for a variety of needle interventions. Combined with ultrasound, the use of photoacoustic imaging can provide the location of needles in tissue, while also visualizing the structure or morphology of the tissue in ultrasound. Furthermore, the present example shows that there is a possibility of differentiating surrounding tissue composition through photoacoustic imaging of needles, even in cases when the optical absorption of tissue may be relatively low and the tissue composition cannot be determined through spectroscopic photoacoustic techniques.

Example 5

Photoacoustic Imaging of Prostate Brachytherapy Seeds

Currently, the standard of care for the guidance of brachytherapy seed implantation is transrectal ultrasound (TRUS), which can gain imaging access to the prostate given the gland's adjacency to the rectal wall and its modest size, with a mean±SD diameter (i.e., height or width dimension), according to a study by Hricak et al., of 4.3±1.0 cm for men (n=15) aged 52-67 years. Since visualization of the small seeds can be difficult, the ultrasound-derived position of the needles—and not the seeds themselves—is often relied upon to infer seed placement. Acoustic shadowing from microcalcifications, off-axis seed placement (i.e., where the ultrasound beam widens), and placement in specific regions of the prostate (e.g., in the periprostatic region, which can have a similar echogenicity to the seeds) can make visualization of seeds with TRUS difficult. Additionally, the acoustic signal generated by a seed is highly dependent on its orientation, with seeds oriented with their long axis perpendicular to the beam more apt to being detected. Given the difficulty in accurately visualizing seeds with TRUS, CT imaging is typically utilized for post-implant dosimetric evaluations. Seed placement that deviates from the dosimetric treatment plan can result in underdosed cancerous regions, requiring postoperative dose corrections through external-beam radiation therapy [3]. Needle deflections of only 5° from the insertion angle decrease the minimum target dose by 10%, thus increasing the tumor-cell survival rate by a factor of 200.

Materials and Methods

To test the feasibility of US and PA to image brachytherapy seeds, several imaging studies were conducted using non-reactive, stainless steel, iodine-125 brachytherapy seeds (IsoAid LLC, Port Richey, Fla.). Combined US and PA imaging studies were performed using a Cortex ultrasound imaging system (Winprobe Corp., North Palm Beach, Fla.) that was interfaced with a 7-MHz center frequency, 14-mm-wide, 128-element linear array transducer (L7, Acuson Corp., Mountain View, Calif.). An Nd:YAG pump laser (Quanta-Ray PRO-290-10, Newport Corp., Irvine, Calif.) with OPO laser output (premiScan/BB 650 OPO, Newport Corp., Irvine, Calif.) and a nominal pulse width of 5 ns was synchronized to the ultrasound acquisition system to optically illuminate the sample in which the seed was embedded. The imaging system was capable of acquiring co-registered PA and US images.

In the first experiment (i.e., the "angular dependence experiment"), the angular dependence of the US and PA signals on seed orientation was investigated. A non-reactive brachytherapy seed was embedded in 8% gelatin at 45° relative to the horizontal (FIGS. 27A and 27C). In an effort to evaluate the seed independently from background influences, acoustic/optical scatterers were not added to the gelatin phantom. A mechanical stage was configured to rotate the transducer from 45° to 135° (relative to the same horizontal reference) in 15° increments. This allowed the long axis of the seed to be imaged at angles from 0° to 90° relative to the transducer face. Both the gelatin phantom and the transducer face were immersed in deionized water to provide acoustic coupling. The seed was placed at the fulcrum of the transducer's rotation to ensure that the seed remained in approximately the same location in the transducer's field of view through the 90° rotation. The laser was operated at 800 nm for PA imaging and was delivered to the sample using a single optical fiber; the fiber had a diameter of 1.5 mm, an NA of 0.39, and was positioned at an oblique angle to the US beam axis (FIGS. 27A and 27B). During the experiment, the laser irradiation position was not altered—the optical fiber and seed were held fixed while only the transducer was rotated—in order to demonstrate that signal changes were due only to the positioning of the transducer relative to the seed.

In a second experiment (i.e., the "bare seed spectrum experiment"), the spectrum of a bare seed's PA signal was established. A non-reactive seed was embedded in a block of 8% gelatin and centered in the imaging plane with US imaging (using the aforementioned system/transducer). PA images of the seed were then obtained from 750 to 1090 nm in 20-nm increments, including 1064 nm. The extinction spectrum of the gelatin alone was analyzed using a UV-VIS-NIR spectrophotometer (UV-3600, Shimadzu Corp., Kyoto, Japan) and found to not significantly influence multi-wavelength PA imaging within the spectrum utilized for testing.

A third experiment (i.e., the "prostate tissue experiment") was performed to examine combined US and PA imaging of brachytherapy seeds in a more realistic environment. In this experiment, five seeds were embedded into five excised bovine prostate samples, which were imaged within 24 hours of each animal's sacrifice, were never frozen, and were cut to be cubical in shape. The proximal tip of each seed was buried approximately 1 mm below the surface of the tissue at varied distances away from each sample's edge (see white scale in FIG. 28A). Each prostate sample was then cast in gelatin to prevent tissue discoloration or deterioration due to water immersion. The first of the five samples was oriented so that the seed's long axis was perpendicular to the US transducer face ("Short-axis Orientation" in FIG. 28B). This orientation was chosen to provide a minimum irradiation path through the prostate tissue of 1 mm, a depth that was too shallow to achieve in the long-axis orientation. For this comparison, multi-wavelength PA imaging, from 750 to 1090 nm, was performed. The other four samples were then oriented so that the seed's long axis was positioned parallel to the US transducer face ("Long-axis Orientation" in FIG. 28B). Using US visualization, the depth of each seed from the sample's edge was determined. Four irradiation path lengths were investigated—4, 10, 13, and 17 mm—while PA images were acquired from 750 to 1090 nm in 40-nm increments, including 1064 nm. Note that PA and US beams were orthogonal to one another and were made to penetrate comparable depths into the tissue (i.e., when the irradiation path was increased, the US propagation path was increased accordingly).

For the second and third experiments, laser irradiation was delivered using an air beam directed at the seed. In all experimentation, laser fluences were measured for each imaging trial, and the mean (n=500 pulses) energy was used to normalize the PA amplitude. Standard deviation of the laser fluence was also used to calculate standard error in the PA amplitude at each wavelength.

For quantitative analysis, PA signal energies were calculated using a kernel surrounding the maximum signal from the seed. The kernel was determined by choosing a region of interest (ROI) with pixel values above a certain threshold in the B-mode image, which corresponded to the location of the seed. This region could be visually verified as the location of the seed due to the presence of the comet-tail artifact, which is present in US imaging of metals, that was located distally from the aforementioned ROI. Data points within the kernel were averaged and normalized according to the mean laser fluence obtained during each trial. For contrast calculations, data kernels (0.6×0.4 mm) for the signal and background ROIs were chosen in order to obtain kernels containing only the respective signal and background measurements. The size of the kernel did not significantly affect contrast calculations as long as each kernel only contained these signal or background measurements. Several contrast values were obtained by translating the position of the signal kernel through the region of the seed (identified by the US image); a corresponding background kernel was similarly translated through an adjacent tissue region located outside the region of the seed. These values were then averaged together to obtain a single reported contrast value in US imaging and at each imaging wavelength in PA imaging. Contrast was calculated according to equation 3 below:

$$\text{Contrast} = \frac{\overline{S}_s - \overline{S}_b}{\overline{S}_b}, \quad (3)$$

where $\overline{S}_s$ and $\overline{S}_b$ are the mean signals from a region within the seed and adjacent background, respectively.

Results

In the angular dependence experiment, combined PA and US images of the brachytherapy seed were acquired from 0° to 90°, in 15° increments. In both the PA and US images, the seed remained visible as the transducer was rotated. In the US images (grayscale images in FIG. 29), when the seed was oriented at 0° relative to the horizontal, the entire seed was visible. A large comet-tail artifact was also visible due to reverberation of the acoustic signal within the seed. As the transducer was rotated, the acoustic signal weakened from the midsection of the seed, while the distal and proximal tips of the seed remained apparent. Through the full rotation, the peak US signal decreased by 13%, with the majority of that decrease occurring between 0° and 30°.

Similar results were observed in the PA images of the seed (yellow-red colormap images in FIG. 29), where the 0° orientation offered the best visualization of the full seed. The body of the seed was still visible when rotated to an angle of 15° from the transducer; however, the signal diminished dramatically after that, as seen in rotation angles of 30° and greater. Much like the US images, comet-tail artifacts are present in the PA images. Unlike the US imaging results, however, only the proximal tip of the seed was clearly apparent through the full rotation of the transducer. Through the full rotation, the peak PA signal decreased by 46%, with the majority of that decrease occurring between 15° and 30°.

In the bare seed spectrum experiment, a seed embedded in pure gelatin was imaged with multi-wavelength PA imaging in order to determine the PA spectrum of the seed alone (square in FIG. 30A). The normalized PA signal was plotted with respect to wavelength. The calculated spectrum presented a monotonically decreasing PA signal with increased laser wavelength, with an approximately 80% reduction in PA signal from 750 to 1090 nm.

The third experiment involved inserting non-reactive seeds into excised bovine prostate tissue. FIG. 30A (circle) offers the PA spectrum of the seed shallowly embedded (short-axis orientation) in prostate tissue. Although the normalized PA signal tends to decrease with wavelength much like the bare seed (square in FIG. 30A), local minima in signal are observed from 950 to 1010 nm, while a local maximum is observed at 1050 nm. FIG. 30B shows the contrast spectrum for this seed in the short-axis orientation, with a peak (average) PA contrast of 40.1 dB (at 810 nm) compared to an average US contrast of 14.3 dB. FIG. 31 shows the combined PA and US images obtained in the long-axis orientation from the 4-mm imaging depth. In the US image (FIG. 31A), background speckle is visible throughout the prostate tissue, with the proximal tissue-gelatin boundary clearly visible at 1.2-1.5 cm axially and the sample's edge visible at the 4-mm lateral position. Although a hyperechoic region is visible at the seed location (i.e., 2.4 cm), the speckle signal from the surrounding tissue reduces overall contrast. A PA image (FIG. 31B) obtained at the same position presents a strong acoustic signal from the seed location, but little acoustic signal is present in the surrounding tissue, resulting in a significant improvement in contrast. By combining FIGS. 31A and 31B, the co-registered images (FIG. 31C) are able to more clearly display the presence of the brachytherapy seed within the tissue background.

Figures 32A, 32B, 32C, 32D, 32E, 32F:
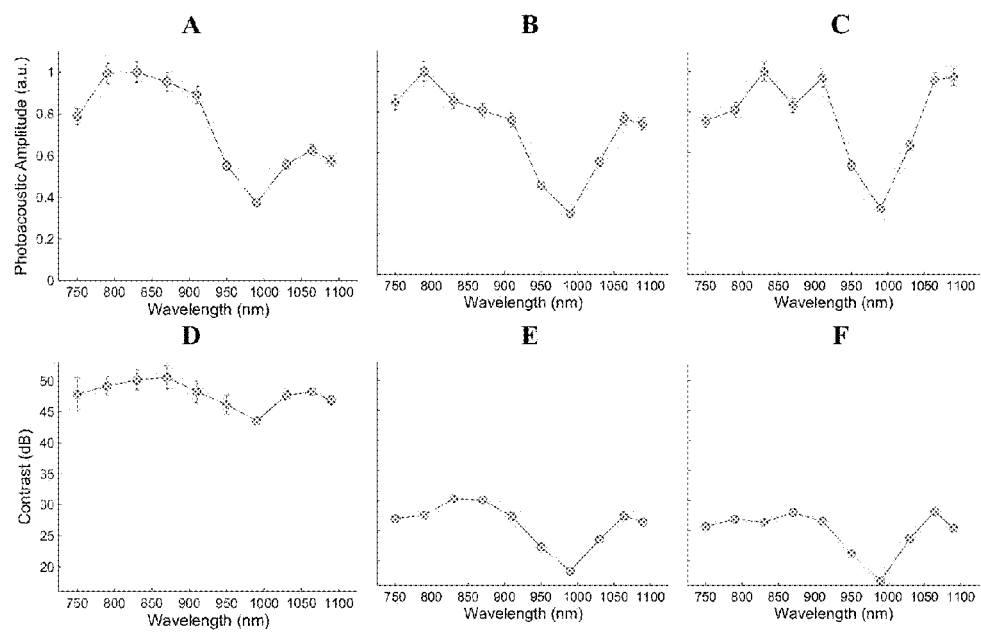

Lastly, the seed was successfully imaged with three different irradiation path lengths, and the PA signal spectrum of each was calculated at nine wavelengths (FIG. 32A-32C). Note that the seed could not be visualized at 17 mm with the utilized fluences, which were similar to those used for imaging at the three shallower depths. For the other three depths (i.e., 4, 10, and 13 mm), a local maximum of the normalized PA signal exists at 1064 nm, while a local minimum can be observed at 990 nm. PA amplitudes for the 10-mm (b) and 13-mm (c) acquisitions decreased, on average, by 93% and 94%, respectively, when compared to the average PA amplitude of the 4-mm (a) acquisition. FIGS. 32D-32F present the contrast values across the acquired spectrum for the three imaging depths. Peak (average) PA contrasts were 50.6 dB (at 870 nm), 30.3 dB (at 830 nm), and 28.2 dB (at 1064 nm), while average US contrasts were 22.7 dB, 24.7 dB, and 25.5 dB for the 4-mm, 10-mm, and 13-mm acquisitions, respectively. Surface fluences were measured (mean±SD) across the acquired spectrum to be 21.7±2.3, 23.6±3.1, and 22.5±5.1 mJ/cm$^2$ for the 4-mm, 10-mm, and 13-mm acquisitions, respectively; fluences tended to decrease with increased wavelength. Specifically, at a wavelength of 1064 nm, surface fluences were measured to be 19.7±0.9, 21.3±0.9, and 20.1±0.8 mJ/cm$^2$ for the aforementioned acquisition depths, respectively.

Discussion

PA imaging of brachytherapy seeds embedded in prostate tissue yielded an improvement of at most 27.9 dB in contrast over conventional US imaging, while seeds were successfully visualized at depths of up to 13 mm. Much like US imaging, PA imaging results were dependent on seed orientation.

In the angular dependence experiment, US imaging results were similar to those observed by Davis et al., with the 0° orientation affording the greatest and most uniform acoustic signal. (B. J. Davis, R. R. Kinnick, M. Fatemi, E. P. Lief, R. A. Robb, and J. F. Greenleaf, "Measurement of the ultrasound backscatter signal from three seed types as a function of incidence angle: Application to permanent prostate brachytherapy," Int. J. Radiat. Oncol. 57, 1174-1182 (2003)). This orientation maximizes the seed's surface area that is perpendicular to and within the path of the acoustic wave transmission, which maximizes backscattered energy. Because the seed becomes an acoustic source when excited by the PA effect, PA imaging yielded very similar rotation results. Due to the seed's capsular geometry, the directivity pattern of the acoustic energy emanating from the seed yields the greatest energy at points normal to the seed's cylindrical midsection. If evenly irradiated, acoustic energy will radiate outward from the seed body. This explains why only the proximal tip of the seed is well visualized in PA imaging as the distal tip, which is rotated away from the transducer face, will tend to transmit energy in the opposing direction.

In the bare seed spectrum experiment, the PA signal spectrum of a bare seed was found to monotonically decrease with increasing laser wavelength. The general trend of decreased absorption with increased wavelength observed in the spectrum for chromium-oxide (solid turquoise line) is consistent with the similar decrease in PA signal—which is proportional to optical absorption—observed in this example. When the seed was shallowly embedded in prostate tissue, however, the generated PA signal spectrum has local minima from 950 to 1010 nm. This phenomenon is likely related to the "environmental" effect of the surrounding tissue (optical) properties on the seed's PA signal. Though the PA signal amplitude is directly related to the optical absorption coefficient of the metallic seed, local fluence is also dependent on the optical absorption and scattering coefficients of the surrounding tissue, resulting in a nonlinear dependence of the PA signal on tissue properties.

In the depth dependence results, contrast plots (FIGS. 32D-32F) were found to have local maxima at 1064 nm, with the deepest acquisition (13 mm) having its absolute maximum at this wavelength as well. Such a result is counter to what the results in the bare seed spectrum experiment might suggest should occur (i.e., given that the PA signal was greatest at 750 nm for the bare seed). In studies of human prostate, scattering has been identified as the dominant loss mechanism and has been found to decrease with increasing irradiation wavelength; this is typical for most soft tissues. Though the optical absorption of metal also decreases with increasing wavelength, the reduction of this absorption with increased wavelength is likely more modest than the decrease in local fluence that results from scattering at lower wavelengths. Given that the obtained PA signal is directly proportional to both optical absorption and local fluence, increasing imaging depth—which reduces local fluence but has no effect on optical absorption—appears to favor higher wavelengths. A local minimum in all of the spectra is observed at 990 nm, a phenomenon which is consistent with the more finely sampled spectrum (circle in FIG. 30A) acquired for the shallowly embedded seed and is likely a consequence of the trade-off between the absorption/scattering properties of the prostate tissue and the decreasing absorption of metal with increasing wavelength.

Contrast values obtained from the PA images of the seed in prostate tissue (FIGS. 30B and 32D-32F) highlight the importance of local fluence and seed orientation on seed visualization. Firstly, a significant decrease in contrast was observed from the 4-mm imaging depth (50.6 dB) to the 10-mm and 13-mm imaging depths (30.3 dB and 28.2 dB, respectively). This decrease is likely due to the drastic reduction in local fluence that results from increased scattering occurring through deeper interrogation regions; this notion is supported by over 90% reductions in PA signals for these deeper interrogations despite surface fluences that were comparable to those used for the shallower, 4-mm interrogation. Additionally, contrast appears to be affected by seed orientation. For the shallowly embedded seed that was imaged in the short-axis orientation (FIG. 30B), a 10.5-dB reduction in peak contrast was observed between it and the 4-mm, long-axis orientation (FIG. 32D). This reduction is due in large part to the nearly 50% reduction in PA signal experienced with the rotation of the brachytherapy seed. Such a signal reduction—which also occurs but to a lesser extent for US imaging—would have resulted in US imaging slightly outperforming PA imaging (i.e., with theoretical contrasts of 24.3 dB and 22.9 dB, respectively) for the 13-mm acquisition had the seed been imaged in the short-axis orientation. For the 4-mm acquisition, theoretical contrast calculations suggest that PA imaging would have still outperformed US imaging had the seed been imaged in the short-axis orientation, with a slightly reduced contrast improvement (i.e., PA imaging over US imaging) of 24.4 dB (compared to a 27.9-dB improvement) being realized in this case. A study by Corbett et al. found, however, that the majority of seeds are placed approximately parallel (i.e., ±16°) to the transducer face during a clinical procedure. (J. F. Corbett, J. J. Jezioranski, J. Crook, T. Tran, and I. W. T. Yeung, "The effect of seed orientation deviations on the quality of 125 i prostate implants," Phys. Med. Biol. 46, 2785 (2001)). Thus, although the case of short-axis imaging is an important one to consider, seeds tend to be oriented for optimal PA imaging. Ultimately, to obtain an appreciable contrast gain in any orientation and fully realize PA imaging's potential in this application, adequate local fluence at the seed location must be achieved.

As previously noted, it was not possible to image a brachytherapy seed at a depth of 17 mm in the prostate tissue sample due to insufficient local fluence. In an effort to increase local fluence in a clinical setting, a fiber optic-based light delivery system could be introduced through a patient's urethra. This would provide an additional irradiation source from within the tissue. With the urethra running through the prostate, maximum irradiation path lengths would be on the order of the prostate's radius (i.e., half the width or height dimension), which was found to have a mean of 21 mm in a study of men aged 52-67 years. (H. Hricak, R. Jeffrey, G. Dooms, and E. Tanagho, "Evaluation of prostate size: A comparison of ultrasound and magnetic resonance imaging," Urol. Radiol. 9, 1-8 (1988)). Consequently, as clinical application of this technology requires imaging beyond the 13 mm demonstrated herein, the use of higher energies and reduced tissue scattering at 1064 nm could be critical in an effort to achieve clinical utilization. In clinical settings, at 1064 nm the American National Standards Institute (ANSI) allows for maximum safe laser fluences of 100 mJ/cm$^2$ compared to 20 mJ/cm$^2$ at <700 nm when imaging through skin. (American National Standards Institute, *ANSI Z136.1-2007 American national standard for safe use of lasers* (2007)). Although there is not currently a specific fluence regulation for irradiation through either the rectal or urethral wall, the aforementioned ANSI limit for skin is likely a conservative estimate for what would be allowed for this application given the relatively high absorption of skin. Based on this limit, a five-fold increase in surface fluence would be allowed in this example. Additionally, it might also be possible to increase local fluence by increasing the laser's pulse width. From a practical standpoint, the primary wavelength of an Nd:YAG laser is 1064 nm, making systems capable of imaging at this wavelength readily available and relatively inexpensive.

The rotation results from the first experiment demonstrate that PA imaging typically does not improve visualization of the full seed. When the seed is not approximately parallel to the transducer face, only the distal tip of the seed can be visualized with PA imaging, while both tips can be visualized with US imaging. The true improvement offered by PA imaging is in detecting and locating the seed, as evidenced by as much as a 27.9-dB increase in contrast. In a study by Corbett et al., it was found that when multiple seeds are implanted, the placement of each seed is important in achieving the intended radiation dose distribution while the orientation is not. (J. F. Corbett, J. J. Jezioranski, J. Crook, T. Tran, and I. W. T. Yeung, "The effect of seed orientation deviations on the quality of 125 i prostate implants," Phys. Med. Biol. 46, 2785 (2001)). Thus, PA imaging's enhanced capability of visualizing the location of seeds could improve a clinician's ability to implement a specific treatment plan.

Conclusion

PA imaging promises improved contrast of brachytherapy seeds in tissue, yielding improvements ranging from 2.7 to 27.9 dB in contrast over US imaging alone for seeds in the long-axis orientation and for imaging depths ranging from 4 to 13 mm. Even more drastic than in US imaging, there is an angular dependence of a seed's PA signal, with the orientation having the greatest surface area normal to the acoustic beam direction resulting in the greatest PA signal. To achieve significant contrast improvements in a clinical application, which would call for imaging depths around 20 mm if a dual transurethral-transrectal irradiation source were implemented, greater laser energies at increased wavelengths (e.g., 1064 nm) may need to be utilized to obtain adequate local fluences. Accordingly, combined PA/US imaging shows strong promise in accurately visualizing the seed and surrounding tissue anatomy during brachytherapy seed placement procedures.

Example 6

Silica-Coating-Induced Photoacoustic Imaging Signal Enhancement

Titanium brachytherapy seeds were coated with silica to enhance the acoustic signal they produced during PA imaging. Coated and non-coated (control) seeds were embedded in a transparent gelatin phantom and imaged with a modified (i.e., with PA imaging capability) Vevo 2100 imager to quantify the PA signal enhancement resulting from silica coating. A 2- to 3-fold signal enhancement was observed between coated and non-coated seeds.

Materials and Methods

Titanium brachytherapy seeds (IsoAid LLC, Port Richey, Fla.) were coated in silica using the classic sol-gel reaction mediated by the tetraethyl orthosilicate (TEOS) precursor (note that silica is the conventional name for the coating, but the more precise chemical name is siloxane). Specifically, Ti seeds were suspended in a stirring solution of 6 mL water, 9 mL isopropyl alcohol (IPA), and 3.6 mL of 3 vol % TEOS in IPA. To initiate the reaction, the pH was increased to 11 by adding 3.6 mL of an ammonium hydroxide solution (0.108 mL of 30% ammonium hydroxide in 3.492 mL of IPA). The reaction was kept at room temperature while stirring at 400 rpm for up to 20 hours. Seeds were removed and triple washed with water at various time points during the reaction to obtain varying layers of silica thickness on the Ti surface.

PA imaging studies were performed using a Vevo 2100 ultrasound system (VisualSonics Inc., Toronto, Canada) that was interfaced with a 21-MHz center frequency linear array. An Nd:YAG pump laser (Quanta-Ray PRO-2 90-10, Newport Corp.) with a nominal pulse width of 5 ns was synchronized to the ultrasound acquisition system to optically illuminate the embedded seeds. Ten seeds—seven silica-coated seeds and three non-coated seeds—were arranged into two rows of fives seeds and embedded in 6% gelatin to facilitate PA imaging analysis; a schematic of one of the seed rows is provided in the top panel of FIG. 33. The gelatin phantom with ten embedded seeds was then placed in a tank filled with deionized water to allow for acoustic coupling during imaging. Three-dimensional PA imaging acquisitions were then obtained with the aforementioned imaging system. Imaging was performed at 800, 900, and 1064 nm with average pulse energies of 1.7, 0.9, and 0.3 mJ, respectively. The imaging transducer was translated laterally to nine distinct lateral locations (with both rows of seeds visible in the transducer's field of view for each location) to allow for averaging of independent acquisitions (i.e., N=9 for each seed and wavelength).

Three-dimensional imaging datasets were segmented to provide the mean PA signal for each seed; the mean signal was calculated from a cubic volume that was centered about each seed and that had dimensions approximately equal to the major/minor axes of the capsular seeds. Mean signals for each seed were then divided by the mean signal from a control seed (i.e., non-coated) contained in that seed's row to calculate signal enhancement.

Results and Discussion

The bottom two images of FIG. 33 show the average PA signal produced by two control seeds (the outer two seeds) and three coated seeds (the inner three seeds). The PA images obtained at 1064 nm (middle) and 800 nm (bottom) qualitatively show an increase in the PA signal generation from the coated seeds when compared to the non-coated seeds. A quantitative comparison of these results is offered in FIG. 34, which presents average±SD (N=9) signal enhancement as a function of coating time. An approximately 2- to 3-fold enhancement is observed with the coated seeds. This enhancement increases with coating time until a maximum is reached (at 2.5 hours), at which time the enhancement decreases slightly. It is presumed that silica coating thickness is related to silica coating times. The mechanism for this silica-coating-mediated PA signal enhancement is thought to be thermodynamic in nature.

Example 7

Thermal Intravascular Photoacoustic (tIVPA) Imaging

Materials and Methods
Animal Model

A Watanabe heritable hyperlipidemic (WHHL) rabbit was used as the animal model for atherosclerosis. WHHL rabbits have high LDL levels in circulating blood due to their genetic deficiency of LDL receptors. This type of rabbit can spontaneously develop atherosclerosis in the aorta and coronary arteries. Lipid metabolism and atherosclerotic plaques of WHHL rabbit resemble that of human. Within 12 to 18 months of age, severe plaques build up in the arteries of WHHL rabbits.

In this example, the abdominal aorta procured from a one year old WHHL rabbit was used for tIVPA imaging. Prior to imaging, WHHL rabbit was sacrificed and the segment of the aorta was removed and preserved in saline damped gauze at 4° C. Imaging experiments were performed within 24 hours after sacrificing the rabbit.

Imaging System

To image an excised vessel, a bench top, combined intravascular IVUS/IVPA imaging system was used (FIG. 35). The ex vivo aorta sample was immersed inside a water cuvette filled with saline. A 40 MHz single element IVUS imaging catheter (Boston Scientific, Inc.) was placed inside the vessel lumen. The transducer located at the tip of the imaging catheter was aligned with the optical fiber. The aorta sample was rotated by a stepper motor (Zaber, Inc.) for cross-sectional scanning Each cross-sectional scanning consisted of 256 A-lines. The laser source for IVPA imaging was provided by a tunable optical parametric oscillator (OPO) laser system (Spectra-Physics, Inc.) capable of generating laser pulses of approximately 3-5 ns duration at 10 Hz repetition rate. The energy of each laser pulse was recorded for off-line compensation of the pulse-to-pulse laser energy variation. Once a laser pulse was generated, an analog to digital convertor card (CompuScope 14200, GaGe, Inc.) was triggered sample the radio frequency signal at a 200 MHz sampling rate. After a user defined delay, a pulser/receiver (5073PR, Olympus, Inc.) was triggered for conventional intravascular ultrasound imaging. The system was capable of acquiring co-registered IVPA and IVUS images of the aorta sample in cross-sectional view.

Experimental Protocol

The abdominal aorta sample was imaged ex vivo within 24 hours after sacrificing the WHHL rabbit. During the imaging experiment, the aorta sample was placed inside the water cuvette with one end attached to a fixture connected to the stepper motor (FIG. 35). The temperature of the aorta sample was changed by adding warm saline, and then cooled down with ice. In order to confirm that the temperature-dependent PA responses were consistent and reversible, the increase and decrease in temperature was repeated three times. Tissue temperature was monitored by a digital thermometer placed inside the water cuvette.

Image Processing

IVPA images acquired at two different temperatures were spatially averaged with a kernel size of 266 μm (axial) by 15.5 degree (azimuthal). The kernel size was around five times larger than the axial resolution and two times larger than the azimuthal resolution of IVPA imaging. The relatively large size of the kernel was selected to minimize the effect of the unwanted tissue motion caused by several factors including irregular mechanical rotation of the sample as well as addition of ice or warm saline to the water cuvette. Then, the finite difference of the PA amplitude between the two IVPA images was calculated as:

$$D_{i,j} = \frac{S_{i,j}^{T_2} - S_{i,j}^{T_1}}{(T_1 - T_2) \cdot S_{i,j}^{T_1}}, \quad (4)$$

where $S_{i,j}^T$ is the PA signal amplitude at pixel at temperature T, and $D_{i,j}$ is the resultant finite difference map. The finite difference map was then color-coded to form the tIVPA image, and displayed over the co-registered IVUS image to show the relative location and magnitude of the tIVPA signal in context of vessel morphology.

Results

Rabbit aorta was imaged first at room temperature (25° C.) using combined IVUS/IVPA imaging system. IVPA imaging was performed at 1210 nm wavelength because lipid has a high optical absorption coefficient at this wavelength. Cross-sectional IVUS image of the vessel showed two hypo-echoic regions that corresponded to the location of plaques (yellow arrows in FIG. 36A). The combined IVUS/IVPA image of the same cross-section is presented in FIG. 36B. Strong PA signals present at the plaque region indicated that these plaques were rich in lipid. Strong PA signals were also observed at the periadventitial regions of the aorta. These signals may have originated from the periadventitial fat due to high optical absorption, high surface optical fluence, and subsurface optical fluence due to the refractive index mismatch between saline and arterial tissue. Oil red O stain for lipid, performed on the tissue section adjacent to the imaged cross-section, confirmed that the aorta contained lipid rich plaques in the intimal layer (FIG. 36C).

To observe the temperature dependent PA response, the temperature of the artery was changed from 38° C. to 17.5° C. three times, and PA responses from areas with high PA signal were analyzed. Specifically, four regions within the plaque and the periadventitial sections were identified and PA signals within these regions were averaged. The amplitude of PA signal was then normalized to the maximum amplitude and plotted versus temperature (FIG. 36D). Interestingly, the PA amplitude from periadventitial regions does not change and remained relatively constant with temperature, while the PA amplitude from plaques decreased with increasing temperature. The different trends of the PA amplitude demonstrates that the Grüneisen parameters for lipid in plaques and tissues in the periadventitial region have different temperature dependencies and, therefore, suggests that lipid in plaques may be differentiated based on the tIVPA imaging.

Using IVPA data obtained at 25° C. and 38° C., a finite difference map was calculated based on Equation 4 and a tIVPA image was generated. The regions with decreasing PA amplitude versus temperature ($0.4/13 < D_{i,j} < 0.95/13$) were colored orange, and displayed over the co-registered IVUS image (FIG. 37A). As shown in the tIVPA image (FIG. 37A), the PA responses from plaque regions showed consistently decreasing PA amplitude with temperature while the PA response from the periadventitial regions was different.

Spectroscopic IVPA (sIVPA) imaging at the same cross-section of the aorta was performed within 1210-1230 nm wavelength range. Similar to tIVPA imaging, sIVPA imaging of lipid also successfully delineated lipid-rich regions in the arterial wall (FIG. 37B), confirming that lipid regions in the tIVPA image reflected lipid deposits inside the plaque. Interestingly, compared to the tIVPA image, sIVPA image showed more lipid constituents in the periadventitial layer of the aorta. This difference indicates that although the lipid deposits in plaques and the periadventitial fat have similar optical properties, their Grüneisen parameter and, therefore, temperature dependent PA response are different.

To further investigate the differences of temperature dependent PA responses between lipid in plaques and lipid in adipose tissue, a sample of rabbit abdominal fat was imaged with the combined IVUS/IVPA imaging system (FIG. 35) by placing the tissue sample between the optical fiber and the single element IVUS catheter. PA signals were acquired at various temperatures at 1210 nm wavelength and normalized to the maximum of the amplitude of PA signal. As shown in FIG. 38, the PA amplitude increases slightly within 22° C. to 38° C. temperature range. Such a trend is opposite to the temperature dependence of the PA signal generated by lipid deposits in the plaques (FIG. 36D, red line), therefore confirming that adipose tissue has a different temperature dependent PA response compared to lipid in plaques.

Discussion tIVPA imaging can be used to differentiate tissues, in particular, lipid in atherosclerotic plaques and adipose tissue. With increasing tissue temperature, the PA amplitude of lipid in plaques decreased while the PA amplitude of lipid in periadventitial and abdominal fat remained relatively constant within 20-38° C. temperature range. The different trends of the PA responses indicated that the Grüneisen parameter of lipids from various regions of body have unique temperature dependences. These dependences may result from differences in tissue composition. Adipose tissues mainly consist of triglyceride, whereas lipid deposits in atherosclerotic plaques originate from LDL particles having a low triglyceride concentration, but a high concentration of cholesterol and cholesterol esters. The difference in triglyceride concentration may be the source of tIVPA contrast.

Various factors such as depth- and wavelength-dependent fluence distribution, the small displacement of aorta sample between different cross-sectional scans, and the variability in acoustic pressure and the sensitivity of the IVUS imaging catheter can influence the amplitude of the PA signal. However, these factors do not affect significantly the temperature dependence of the PA response and, therefore, the contrast in tIVPA images.

In clinical practice, the decrease or increase of the temperature of the blood vessel wall may be induced by flushing low temperature fluid, inflating a balloon catheter filled with low temperature fluid, or irradiating the artery wall with laser light, ultrasound or microwaves. Thermal PA imaging of lipid can also be applied to image superficial vessels such as carotid arteries. Finally, thermal PA imaging may also be applied to cancer diagnosis and imaging of other pathologies where lipid plays an important role in disease formation and progression.

In this example, IVPA imaging was performed ex vivo on an atherosclerotic rabbit artery at different temperatures. Different temperature dependencies of PA responses were found in lipid and periadventitial fat. Based on the thermal PA responses, thermal intravascular photoacoustic (tIVPA) imaging was introduced to differentiate lipid in atherosclerotic plaques. The advantage of tIVPA imaging is that it could be performed using an IVPA imaging system operating at a single wavelength. More importantly, tIVPA imaging has the potential to differentiate lipids that have the same optical absorption property and, therefore, may not be distinguishable using conventional photoacoustic imaging approaches.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

1. D. Maintz, R. M. Botnar, R. Fischbach, W. Heindel, W. J. Manning, and M. Stuber, "Coronary magnetic resonance angiography for assessment of the stent lumen: a phantom study," J. Cardiovasc. Magn. Reson. 4(3), 359-367 (2002).
2. D. R. Elgort, C. M. Hillenbrand, S. Zhang, E. Y. Wong, S. Rafie, J. S. Lewin, and J. L. Duerk, "Image-guided and -monitored renal artery stenting using only MRI," J. Magn. Reson. Imaging 23(5), 619-627 (2006).
3. J. Hug, E. Nagel, A. Bornstedt, B. Schnackenburg, H. Oswald, and E. Fleck, "Coronary arterial stents: safety and artifacts during MR imaging," Radiology 216(3), 781-787 (2000).
4. D. Maintz, K. U. Juergens, T. Wichter, M. Grude, W. Heindel, and R. Fischbach, "Imaging of coronary artery stents using multislice computed tomography: in vitro evaluation," Eur. Radiol. 13(4), 830-835 (2003).
5. Y. Kawase, K. Hoshino, R. Yoneyama, J. McGregor, R. J. Hajjar, I. K. Jang, and M. Hayase, "In vivo volumetric analysis of coronary stent using optical coherence tomography with a novel balloon occlusion flushing catheter: a comparison with intravascular ultrasound," Ultrasound Med. Biol. 31(10), 1343-1349 (2005).
6. G. S. Mintz, S. E. Nissen, W. D. Anderson, S. R. Bailey, R. Erbel, P. J. Fitzgerald, F. J. Pinto, K. Rosenfield, R. J. Siegel, E. M. Tuzcu, and P. G. Yock, "American College of Cardiology Clinical Expert Consensus Document on Standards for Acquisition, Measurement and Reporting of Intravascular Ultrasound Studies (IVUS). A report of the American College of Cardiology Task Force on Clinical Expert Consensus Documents," J. Am. Coll. Cardiol. 37(5), 1478-1492 (2001).
7. P. Barlis, K. Dimopoulos, J. Tanigawa, E. Dzielicka, G. Ferrante, F. Del Furia, and C. Di Mario, "Quantitative analysis of intracoronary optical coherence tomography measurements of stent strut apposition and tissue coverage," Int. J. Cardiol (2009).
8. T. L. Slottow, R. Pakala, T. Okabe, D. Helling a, R. J. Lovec, F. O. Tio, A. B. Bui, and R. Waksman, "Optical coherence tomography and intravascular ultrasound imaging of bioabsorbable magnesium stent degradation in porcine coronary arteries," Cardiovasc. Revasc. Med. 9(4), 248-254 (2008).
9. I. K. Jang, B. E. Bouma, D. H. Kang, S. J. Park, S. W. Park, K. B. Seung, K. B. Choi, M. Shishkov, K. Schlendorf, E.

Pomerantsev, S. L. Houser, H. T. Aretz, and G. J. Tearney, "Visualization of coronary atherosclerotic plaques in patients using optical coherence tomography: comparison with intravascular ultrasound," *J. Am. Coll. Cardiol.* 39(4), 604-609 (2002).
10. S. Sethuraman, S. R. Aglyamov, J. H. Amirian, R. W. Smalling, and S. Y. Emelianov, "Intravascular photoacoustic imaging using an IVUS imaging catheter," *IEEE Trans. Ultrason. Ferroelectr. Freq. Control* 54(5), 978-986 (2007).
11. S. Sethuraman, J. H. Amirian, S. H. Litovsky, R. W. Smalling, and S. Y. Emelianov, "Ex vivo Characterization of Atherosclerosis using Intravascular Photoacoustic Imaging," *Opt. Express* 15(25), 16657-16666 (2007).
12. S. Sethuraman, J. H. Amirian, S. H. Litovsky, R. W. Smalling, and S. Y. Emelianov, "Spectroscopic intravascular photoacoustic imaging to differentiate atherosclerotic plaques," *Opt. Express* 16(5), 3362-3367 (2008).
13. J. Butany, K. Carmichael, S. W. Leong, and M. J. Collins, "Coronary artery stents: identification and evaluation," *J. Clin. Pathol.* 58(8), 795-804 (2005).
14. B. Wang, A. B. Karpiouk, and S. Y. Emelianov, "Design of catheter for combined intravascular photoacoustic and ultrasound imaging". Proceedings of the 2008 IEEE Ultrasonics Symposium 1150-1153 (2008).
15. D. J. Faber, M. C. Aalders, E. G. Mik, B. A. Hooper, M. J. van Gemert, and T. G. van Leeuwen, "Oxygen saturation-dependent absorption and scattering of blood," *Phys. Rev. Lett.* 93(2), 028102 (2004).
16. J. W. Charboneau, C. C. Reading, and T. J. Welch, "CT and sonographically guided needle biopsy: current techniques and new innovations," *Am. J. Roentgenol.* 154, 1-10 (1990).
17. G. A. Chapman, D. Johnson, and A. R. Bodenham, "Visualisation of needle position using ultrasonography," *Anaesthesia* 61, 148-158 (2006).
18. K. J. Chin, A. Perlas, V. W. Chan, and R. Brull, "Needle visualization in ultrasound-guided regional anesthesia: challenges and solutions," *Reg. Anesth. Pain Med.* 33, 532-544 (2008).
19. N. Abolhassani, R. V. Patel, and F. Ayazi, "Minimization of needle deflection in robot-assisted percutaneous therapy," *Int J. Med. Robot* 3, 140-148 (2007).
20. S, Nath, Z. Chen, N. Yue, S. Trumpore, and R. Peschel, "Dosimetric effects of needle divergence in prostate seed implant using 125I and 103Pd radioactive seeds," *Med. Phys.* 27, 1058-1066 (2000).
21. I. Schafhalter-Zoppoth, C. E. McCulloch, and A. T. Gray, "Ultrasound visibility of needles used for regional nerve block: an in vitro study," *Reg. Anesth. Pain Med.* 29, 480-488 (2004).
22. T. Hatada, H. Ishii, S. Ichii, K. Okada, and T. Yamamura, "Ultrasound-guided fine-needle aspiration biopsy for breast tumors: needle guide versus freehand technique," *Tumori* 85, 12-14 (1999).
23. P. M. Phal, D. M. Brooks, and R. Wolfe, "Sonographically guided biopsy of focal lesions: a comparison of freehand and probe-guided techniques using a phantom," *Am. J. Roentgenol.* 184, 1652-1656 (2005).
24. M. C. Ziskin, D. I. Thickman, N.J. Goldenberg, M. S. Lapayowker, and J. M. Becker, "The comet tail artifact," *J. Ultrasound Med.* 1, 1-7 (1982).
25. A. Gronningsaeter, T. Lie, K. Bolz, and A. Heimdal, "Ultrasonographic stent-imaging artifacts," *J. Vasc. Invest.* 1, 140-149 (1995).
26. G. Finet, C. Cachard, P. Delachartre, E. Maurincomme, and J. Beaune, "Artifacts in intravascular ultrasound imaging during coronary artery stent implantation," *Ultrasound Med. Biol.* 24, 793-802 (1998).
27. K. Homan, J. Shah, S. Gomez, H. Gensler, A. B. Karpiouk, L. Brannon-Peppas, and S. Y. Emelianov, "Combined ultrasound and photoacoustic imaging of pancreatic cancer using nanocage contrast agents," in *Proc. 2009 SPIE Photonics West Symposium: Photons Plus Ultrasound: Imaging and Sensing, Proc. SPIE* 71771M, (2009).
28. S. Mallidi, T. Larson, J. Tam, P. P. Joshi, A. Karpiouk, K. Sokolov, and S. Emelianov, "Multiwavelength photoacoustic imaging and plasmon resonance coupling of gold nanoparticles for selective detection of cancer," *Nano Lett.* 9, 2825-2831 (2009).
29. S. Park, S. R. Aglyamov, W. G. Scott, and S. Y. Emelianov, "Strain imaging using conventional and ultrafast ultrasound imaging: numerical analysis," *IEEE Trans. Ultrason. Ferroelectr. Freq. Control* 54, 987-995 (2007).
30. T. Varghese and J. Ophir, "An analysis of elastographic contrast-to-noise ratio," *Ultrasound Med. Biol.* 24, 915-924 (1998).
31. S. Sethuraman, J. H. Amirian, S. H. Litovsky, R. W. Smalling, and S. Y. Emelianov, "Spectroscopic intravascular photoacoustic imaging to differentiate atherosclerotic plaques," *Opt. Express* 16, 3362-3367 (2008).
32. J. Butany, K. Carmichael, S. W. Leong, and M. J. Collins, "Coronary artery stents: identification and evaluation," *J. Clin. Pathol.* 58, 795-804 (2005).
33. Z. Wei, M. Ding, D. Downey, and A. Fenster, "3D TRUS guided robot assisted prostate brachytherapy," *Med. Image Comput. Comput. Assist. Interv.* 8, 17-24 (2005).
34. J. L. Su, B. Wang, and S. Y. Emelianov, "Photoacoustic imaging of coronary artery stents," *Opt. Express* 17, 19894-19901 (2009).
35. M. Morooka, K. Kubota, Y. Kono, K. Ito, K. Kurihara, T. Mitsumoto, T. Sato, Y. Oshiro, T. Aruga, K. Hasuo, M. Kanemura, and S. Minowada, "Scintigraphic detection of I-125 seeds migration after permanent brachytherapy for prostate cancer: how far do seeds travel?," *Clin. Nucl. Med.* 34, 466-469 (2009).
36. M. Tavakoli, E. J. Kellar, D. Nassiri, and A. E. Joseph, "A novel polymeric coating for enhanced ultrasound visibility of medical devices," *Med Device Technol* 17, 8-10, 12, (2006).

What is claimed is:

1. A method comprising:
exposing at least a portion of a sample comprising a metal object to electromagnetic radiation so as to generate an acoustic response;
detecting the acoustic response with an acoustic sensor;
generating a photoacoustic image of at least the portion of the sample comprising the metal object based on the acoustic response detected by the acoustic sensor;
exposing at least a portion of the sample comprising the metal object to an acoustic sound wave so as to generate an echo;
detecting the echo with the acoustic sensor; and
generating an ultrasound image of at least the portion of the sample comprising the metal object based on the echo detected by the acoustic sensor.

2. The method of claim 1 further comprising determining the location or positioning of the metal object within the sample by using an overlay of the photoacoustic image and the ultrasound image.

3. The method of claim 2 further comprising determining the composition of the biological tissue using the photoacoustic enhancement effect of the Grüneisen coefficient.

4. The method of claim 1 wherein the sample comprises biological tissue.

5. The method of claim 4 further comprising at least partially determining the composition of the biological tissue proximate to at least a portion of the metal object based on the acoustic response detected by the acoustic sensor.

6. The method of claim 1 wherein the metal object comprises at least one metal object selected from the group consisting of: a coronary artery stent, a needle, a brachytherapy seed, a surgical staple and an orthopedic implant.

7. The method of claim 1 wherein exposing at least a portion of the sample comprising the metal object to electromagnetic radiation comprises exposing at least a portion of the sample to a pulsed laser.

8. The method of claim 7 comprising exposing the sample to pulses of electromagnetic radiation from the pulsed laser, the pulses having a duration of 1 nanoseconds to 1000 ns.

9. The method of claim 1 wherein the electromagnetic radiation has a wavelength of approximately 808 nanometers or approximately 1064 nanometers.

10. The method of claim 1 further comprising:
exposing the sample comprising the metal object to more than one wavelength of electromagnetic radiation so as to generate a series of acoustic responses;
detecting the series of acoustic responses with the acoustic sensor; and
relating the series of acoustic responses to the optical absorption of the metal object so as to generate the photoacoustic image.

11. The method of claim 10 wherein the more than one wavelength of electromagnetic radiation comprises at least two different wavelengths from 500 to 1200 nanometers.

12. The method of claim 1 wherein the acoustic sensor comprises an ultrasonic transducer.

13. The method of claim 1 wherein the metal object comprises a coating that alters a thermodynamic or optical property of the metal object so as to enhance the acoustic response generated when the metal object is exposed to electromagnetic radiation.

14. The method of claim 13 wherein the coating comprises at least one selected from the group consisting of: silica, gold, metal nanoparticles, and metal nanoparticles coated in silica.

15. The method of claim 1 wherein the method occurs in real time.

16. The method of claim 1 wherein the electromagnetic radiation has a wavelength of approximately 500 nanometers or approximately 1200 nanometers.

17. The method of claim 1 wherein the electromagnetic radiation has a wavelength of approximately 700 nanometers or approximately 1100 nanometers.

18. The method of claim 1 wherein all exposing and detecting steps are carried out using an intravascular ultrasound (IVUS)/intravascular photoacoustic (IVPA) imaging device.

19. The method of claim 1 wherein the IVUS/IVPA imaging device is a catheter-based imaging device.

\* \* \* \* \*